(12) United States Patent
Licata

(10) Patent No.: US 8,579,954 B2
(45) Date of Patent: Nov. 12, 2013

(54) UNTWISTING RESTRAINT IMPLANT DELIVERY SYSTEM

(75) Inventor: David Licata, Menlo Park, CA (US)

(73) Assignee: Biosensors International Group, Ltd., Hamilton (BM)

( * ) Notice: Subject to any disclaimer, the term of this patent is extended or adjusted under 35 U.S.C. 154(b) by 1796 days.

(21) Appl. No.: 11/342,316

(22) Filed: Jan. 27, 2006

(65) Prior Publication Data

US 2007/0100417 A1 May 3, 2007

Related U.S. Application Data

(63) Continuation of application No. 11/265,999, filed on Nov. 2, 2005.

(51) Int. Cl.
*A61F 2/06* (2013.01)

(52) U.S. Cl.
USPC .................................. 623/1.11; 623/1.12

(58) Field of Classification Search
USPC ........ 623/1.11, 1.12, 1.23; 606/108, 191, 194
See application file for complete search history.

(56) References Cited

U.S. PATENT DOCUMENTS

| | | | |
|---|---|---|---|
| 4,503,569 A | 3/1985 | Dotter | |
| 4,512,338 A | 4/1985 | Balko et al. | |
| 4,553,545 A | 11/1985 | Maass et al. | |
| 4,562,596 A | 1/1986 | Kornberg | |
| 4,580,568 A | 4/1986 | Gianturco | |
| 4,655,771 A | 4/1987 | Wallsten | |
| 4,665,918 A | 5/1987 | Garza et al. | |
| 4,732,152 A | 3/1988 | Wallsten et al. | |
| 4,733,665 A | 3/1988 | Palmaz | |
| 4,762,128 A | 8/1988 | Rosenbluth | |
| 4,768,507 A | 9/1988 | Fischell et al. | |
| 4,771,773 A | 9/1988 | Kropf | |
| 4,776,337 A | 10/1988 | Palmaz | |
| 4,830,003 A | 5/1989 | Wolff et al. | |
| 4,848,343 A | 7/1989 | Wallsten et al. | |
| 4,875,480 A | 10/1989 | Imbert | |
| 4,878,906 A | 11/1989 | Lindemann et al. | |
| 4,893,623 A | 1/1990 | Rosenbluth | |
| 4,913,141 A | 4/1990 | Hillstead | |

(Continued)

FOREIGN PATENT DOCUMENTS

| | | |
|---|---|---|
| DE | 4420142 | 12/1995 |
| EP | 0667 132 | 8/1995 |

(Continued)

OTHER PUBLICATIONS

Duerig et al., "An overview of superelastic stent desing" Min Invas Ther & Allied Technol, 9(3/4):234-246 (2000).

(Continued)

*Primary Examiner* — Dianne Dornbusch
(74) *Attorney, Agent, or Firm* — Kilpatrick Townsend & Stockton LLP

(57) ABSTRACT

Medical devices and methods for delivery or implantation of prostheses within hollow body organs and vessels or other luminal anatomy are disclosed. The subject technologies may be used in the treatment of atherosclerosis in stenting procedures or be used in variety of other procedures. The systems may employ a self expanding stent restrained by one or more members released by an electrolytically erodable latch. Such release means do not connect directly to the implant, though one or more portions may contact it.

9 Claims, 23 Drawing Sheets

(56) References Cited

U.S. PATENT DOCUMENTS

| | | | |
|---|---|---|---|
| 4,950,227 | A | 8/1990 | Savin et al. |
| 4,954,126 | A | 9/1990 | Wallsten |
| 4,969,890 | A | 11/1990 | Sugita et al. |
| 4,990,151 | A | 2/1991 | Wallsten |
| 4,990,155 | A | 2/1991 | Wilkoff |
| 4,998,539 | A | 3/1991 | Delsanti |
| 5,019,085 | A | 5/1991 | Hillstead |
| 5,019,090 | A | 5/1991 | Pinchuk |
| 5,026,377 | A | 6/1991 | Burton et al. |
| 5,035,706 | A | 7/1991 | Giantureo et al. |
| 5,061,275 | A | 10/1991 | Wallsten et al. |
| 5,064,435 | A | 11/1991 | Porter |
| 5,067,957 | A | 11/1991 | Jervis |
| 5,071,407 | A | 12/1991 | Termin et al. |
| 5,089,006 | A | 2/1992 | Stiles |
| 5,092,877 | A | 3/1992 | Pinchuk |
| 5,102,417 | A | 4/1992 | Palmaz |
| 5,108,407 | A | 4/1992 | Geremia et al. |
| 5,108,416 | A | 4/1992 | Ryan et al. |
| 5,122,136 | A | 6/1992 | Guglielmi et al. |
| 5,147,370 | A | 9/1992 | McNamara et al. |
| 5,158,548 | A | 10/1992 | Lau et al. |
| 5,160,341 | A | 11/1992 | Brenneman et al. |
| 5,180,367 | A | 1/1993 | Kontos et al. |
| 5,192,297 | A | 3/1993 | Hull |
| 5,201,757 | A | 4/1993 | Heyn et al. |
| 5,221,261 | A | 6/1993 | Termin et al. |
| 5,242,399 | A | 9/1993 | Lau et al. |
| 5,242,452 | A | 9/1993 | Inoue |
| 5,246,445 | A | 9/1993 | Yachia et al. |
| 5,263,964 | A | 11/1993 | Purdy |
| 5,266,073 | A | 11/1993 | Wall |
| 5,290,305 | A | 3/1994 | Inoue |
| 5,306,294 | A | 4/1994 | Winston et al. |
| 5,320,635 | A | 6/1994 | Smith |
| 5,334,210 | A | 8/1994 | Gianturco |
| 5,354,295 | A | 10/1994 | Guglielmi et al. |
| 5,360,401 | A | 11/1994 | Turnland et al. |
| 5,372,600 | A | 12/1994 | Beyar et al. |
| 5,382,259 | A | 1/1995 | Phelps et al. |
| 5,407,432 | A | 4/1995 | Solar |
| 5,415,664 | A | 5/1995 | Pinchuk |
| 5,423,829 | A | 6/1995 | Pham et al. |
| 5,433,723 | A | 7/1995 | Lindenberg et al. |
| 5,443,477 | A | 8/1995 | Marin et al. |
| 5,445,646 | A | 8/1995 | Euteneuer et al. |
| 5,476,505 | A | 12/1995 | Limon |
| 5,484,444 | A | 1/1996 | Braunschweiler et al. |
| 5,486,195 | A | 1/1996 | Myers et al. |
| 5,507,771 | A | 4/1996 | Gianturco |
| 5,522,836 | A | 6/1996 | Palermo |
| 5,522,883 | A | 6/1996 | Slater et al. |
| 5,534,007 | A | 7/1996 | St. Germain et al. |
| 5,540,680 | A | 7/1996 | Guglielmi et al. |
| 5,554,181 | A | 9/1996 | Das |
| 5,569,245 | A | 10/1996 | Guglielmi et al. |
| 5,571,135 | A | 11/1996 | Fraser et al. |
| 5,578,074 | A | 11/1996 | Mirigian |
| 5,591,196 | A | 1/1997 | Marin et al. |
| 5,601,600 | A | 2/1997 | Ton |
| 5,618,300 | A | 4/1997 | Marin et al. |
| 5,634,928 | A | 6/1997 | Fischell et al. |
| 5,639,274 | A | 6/1997 | Fischell et al. |
| 5,643,254 | A | 7/1997 | Scheldrup et al. |
| 5,653,748 | A | 8/1997 | Strecker |
| 5,683,451 | A | 11/1997 | Lenker et al. |
| 5,690,643 | A | 11/1997 | Wijay |
| 5,690,644 | A | 11/1997 | Yurek et al. |
| 5,702,364 | A | 12/1997 | Euteneuer et al. |
| 5,702,418 | A | 12/1997 | Ravenscroft |
| 5,725,549 | A | 3/1998 | Lam |
| 5,725,551 | A | 3/1998 | Myers et al. |
| 5,733,267 | A | 3/1998 | Del Toro |
| 5,733,325 | A | 3/1998 | Robinson et al. |
| 5,772,609 | A | 6/1998 | Nguyen et al. |
| 5,772,668 | A | 6/1998 | Summers et al. |
| 5,772,669 | A | 6/1998 | Vrba |
| 5,776,141 | A | 7/1998 | Klein et al. |
| 5,776,142 | A | 7/1998 | Gunderson |
| 5,782,838 | A | 7/1998 | Beyar et al. |
| 5,788,707 | A | 8/1998 | Del Toro et al. |
| 5,797,857 | A | 8/1998 | Obitsu |
| 5,797,952 | A | 8/1998 | Klein |
| 5,800,455 | A | 9/1998 | Palermo et al. |
| 5,800,517 | A | 9/1998 | Anderson et al. |
| 5,807,398 | A | 9/1998 | Shaknovich |
| 5,810,837 | A | 9/1998 | Hofmann et al. |
| 5,817,101 | A | 10/1998 | Fiedler |
| 5,824,041 | A | 10/1998 | Lenker et al. |
| 5,824,053 | A | 10/1998 | Khosravi et al. |
| 5,824,054 | A | 10/1998 | Khosravi et al. |
| 5,824,058 | A | 10/1998 | Ravenscroft et al. |
| RE35,988 | E | 12/1998 | Winston et al. |
| 5,843,090 | A | 12/1998 | Schuetz |
| 5,851,206 | A | 12/1998 | Guglielmi et al. |
| 5,855,578 | A | 1/1999 | Guglielmi et al. |
| 5,873,907 | A * | 2/1999 | Frantzen ............... 623/1.11 |
| 5,891,128 | A | 4/1999 | Gia et al. |
| 5,919,187 | A | 7/1999 | Guglielmi et al. |
| 5,919,204 | A | 7/1999 | Lukic et al. |
| 5,919,225 | A | 7/1999 | Lau et al. |
| 5,920,975 | A | 7/1999 | Morales |
| 5,941,888 | A | 8/1999 | Wallace et al. |
| 5,944,726 | A | 8/1999 | Blaeser et al. |
| 5,948,017 | A | 9/1999 | Taheri |
| 5,957,930 | A | 9/1999 | Vrba |
| 5,968,052 | A | 10/1999 | Sullivan et al. |
| 5,980,485 | A | 11/1999 | Grantz et al. |
| 5,980,514 | A | 11/1999 | Kupiecki et al. |
| 5,980,530 | A | 11/1999 | Willard et al. |
| 5,984,929 | A | 11/1999 | Bashiri et al. |
| 5,989,242 | A | 11/1999 | Saadat et al. |
| 5,989,280 | A | 11/1999 | Euteneuer et al. |
| 6,004,328 | A | 12/1999 | Solar |
| 6,015,429 | A | 1/2000 | Lau et al. |
| 6,019,737 | A | 2/2000 | Murata |
| 6,019,779 | A | 2/2000 | Thorud et al. |
| 6,027,516 | A | 2/2000 | Kolobow et al. |
| 6,027,520 | A | 2/2000 | Tsugita et al. |
| 6,042,588 | A | 3/2000 | Munsinger et al. |
| 6,042,589 | A | 3/2000 | Marianne |
| 6,042,605 | A | 3/2000 | Martin et al. |
| 6,048,360 | A | 4/2000 | Khosravi et al. |
| 6,053,940 | A | 4/2000 | Wijay |
| 6,056,759 | A | 5/2000 | Fiedler |
| 6,059,779 | A | 5/2000 | Mills |
| 6,059,813 | A | 5/2000 | Vrba et al. |
| 6,063,101 | A | 5/2000 | Jacobsen et al. |
| 6,063,104 | A | 5/2000 | Villar et al. |
| 6,068,634 | A | 5/2000 | Lorentzen Cornelius et al. |
| 6,068,644 | A | 5/2000 | Lulo et al. |
| 6,071,286 | A | 6/2000 | Mawad |
| 6,077,297 | A | 6/2000 | Robinson et al. |
| 6,093,194 | A | 7/2000 | Mikus et al. |
| 6,096,034 | A | 8/2000 | Kupiecki et al. |
| 6,096,045 | A | 8/2000 | Del Toro et al. |
| 6,102,942 | A | 8/2000 | Ahari |
| 6,113,608 | A | 9/2000 | Monroe et al. |
| 6,117,140 | A | 9/2000 | Munsinger |
| 6,120,522 | A | 9/2000 | Vrba et al. |
| 6,123,714 | A | 9/2000 | Gia et al. |
| 6,123,720 | A | 9/2000 | Anderson et al. |
| 6,126,685 | A | 10/2000 | Lenker et al. |
| 6,139,524 | A | 10/2000 | Killion |
| 6,139,564 | A | 10/2000 | Teoh |
| 6,156,061 | A | 12/2000 | Wallace et al. |
| 6,156,062 | A | 12/2000 | McGuinness |
| 6,161,029 | A | 12/2000 | Spreigl et al. |
| 6,165,178 | A | 12/2000 | Bashiri et al. |
| 6,168,529 | B1 | 1/2001 | Moulinet |
| 6,168,579 | B1 | 1/2001 | Tsugita |
| 6,168,592 | B1 | 1/2001 | Kupiecki et al. |
| 6,168,616 | B1 | 1/2001 | Brown, III |
| 6,168,618 | B1 | 1/2001 | Frantzen |

(56) References Cited

U.S. PATENT DOCUMENTS

| | | |
|---|---|---|
| 6,174,327 B1 | 1/2001 | Mertens et al. |
| 6,183,481 B1 | 2/2001 | Lee et al. |
| 6,183,505 B1 | 2/2001 | Mohn, Jr. et al. |
| 6,193,708 B1 | 2/2001 | Ken et al. |
| 6,200,305 B1 | 3/2001 | Berthiaume et al. |
| 6,203,550 B1 | 3/2001 | Olson |
| 6,206,888 B1 | 3/2001 | Bicek et al. |
| 6,214,036 B1 | 4/2001 | Letendre et al. |
| 6,221,081 B1 | 4/2001 | Mikus et al. |
| 6,221,097 B1 | 4/2001 | Wang et al. |
| 6,228,110 B1 | 5/2001 | Munsinger |
| 6,231,598 B1 | 5/2001 | Berry et al. |
| 6,238,410 B1 | 5/2001 | Vrba et al. |
| 6,238,430 B1 | 5/2001 | Klumb et al. |
| 6,241,758 B1 | 6/2001 | Cox |
| 6,245,097 B1 | 6/2001 | Inoue |
| 6,248,122 B1 | 6/2001 | Klumb et al. |
| 6,254,609 B1 | 7/2001 | Vrba et al. |
| 6,254,611 B1 | 7/2001 | Vrba |
| 6,254,628 B1 | 7/2001 | Wallace et al. |
| 6,264,671 B1 | 7/2001 | Stack et al. |
| 6,264,683 B1 | 7/2001 | Stack et al. |
| 6,267,783 B1 | 7/2001 | Letendre et al. |
| 6,270,504 B1 | 8/2001 | Lorentzen Cornelius et al. |
| 6,273,881 B1 | 8/2001 | Kiemeneij |
| 6,280,465 B1 | 8/2001 | Cryer |
| 6,287,331 B1 | 9/2001 | Heath |
| 6,302,893 B1 | 10/2001 | Limon et al. |
| 6,306,141 B1 | 10/2001 | Jervis |
| 6,306,162 B1 | 10/2001 | Patel |
| 6,319,275 B1 | 11/2001 | Lashinski et al. |
| 6,342,066 B1 | 1/2002 | Toro et al. |
| 6,344,041 B1 | 2/2002 | Kupiecki et al. |
| 6,346,118 B1 | 2/2002 | Baker et al. |
| 6,350,277 B1 | 2/2002 | Kocur |
| 6,350,278 B1 | 2/2002 | Lenker et al. |
| 6,361,637 B2 | 3/2002 | Martin et al. |
| 6,368,344 B1 | 4/2002 | Fitz |
| 6,371,962 B1 | 4/2002 | Ellis et al. |
| 6,375,660 B1 | 4/2002 | Fischell et al. |
| 6,379,365 B1 | 4/2002 | Diaz |
| 6,380,457 B1 | 4/2002 | Yurek et al. |
| 6,383,174 B1 | 5/2002 | Eder |
| 6,387,118 B1 | 5/2002 | Hanson |
| 6,391,050 B1 | 5/2002 | Broome |
| 6,391,051 B2 | 5/2002 | Sullivan, III et al. |
| 6,395,017 B1 | 5/2002 | Dwyer et al. |
| 6,409,750 B1 | 6/2002 | Hyodoh et al. |
| 6,409,752 B1 | 6/2002 | Boatman et al. |
| 6,413,269 B1 | 7/2002 | Bui et al. |
| 6,416,536 B1 | 7/2002 | Yee |
| 6,416,545 B1 | 7/2002 | Mikus et al. |
| 6,423,090 B1 | 7/2002 | Hancock |
| 6,425,898 B1 | 7/2002 | Wilson et al. |
| 6,425,914 B1 | 7/2002 | Wallace et al. |
| 6,425,915 B1 | 7/2002 | Khosravi et al. |
| 6,428,489 B1 | 8/2002 | Jacobsen et al. |
| 6,428,566 B1 | 8/2002 | Holt |
| 6,432,080 B2 | 8/2002 | Pederson, Jr. et al. |
| 6,432,129 B2 | 8/2002 | DiCaprio |
| 6,447,540 B1 | 9/2002 | Fontaine et al. |
| 6,448,700 B1 | 9/2002 | Gupta et al. |
| 6,451,025 B1 | 9/2002 | Jervis |
| 6,451,052 B1 | 9/2002 | Burmeister et al. |
| 6,454,795 B1 | 9/2002 | Chuter |
| 6,458,092 B1 | 10/2002 | Gambale et al. |
| 6,468,266 B1 | 10/2002 | Bashiri et al. |
| 6,468,298 B1 | 10/2002 | Pelton |
| 6,468,301 B1 | 10/2002 | Amplatz et al. |
| 6,482,227 B1 | 11/2002 | Solovay |
| 6,485,515 B2 | 11/2002 | Strecker |
| 6,488,700 B2 | 12/2002 | Klumb et al. |
| 6,517,548 B2 | 2/2003 | Lorentzen Cornelius et al. |
| 6,517,569 B2 | 2/2003 | Mikus et al. |
| 6,520,986 B2 | 2/2003 | Martin et al. |
| 6,530,947 B1 | 3/2003 | Euteneuer et al. |
| 6,533,805 B1 * | 3/2003 | Jervis .................... 623/1.11 |
| 6,533,807 B2 | 3/2003 | Wolinsky et al. |
| 6,537,295 B2 | 3/2003 | Petersen |
| 6,558,415 B2 | 5/2003 | Thompson |
| 6,562,063 B1 | 5/2003 | Euteneuer et al. |
| 6,562,064 B1 | 5/2003 | deBeer |
| 6,579,297 B2 | 6/2003 | Bicek et al. |
| 6,579,308 B1 | 6/2003 | Jansen et al. |
| 6,582,460 B1 | 6/2003 | Cryer |
| 6,602,226 B1 | 8/2003 | Smith et al. |
| 6,602,272 B2 | 8/2003 | Boylan et al. |
| 6,607,539 B1 | 8/2003 | Hayashi et al. |
| 6,607,551 B1 | 8/2003 | Sullivan et al. |
| 6,613,079 B1 | 9/2003 | Wolinsky et al. |
| 6,620,152 B2 | 9/2003 | Guglielmi |
| 6,623,518 B2 | 9/2003 | Thompson et al. |
| 6,626,938 B1 | 9/2003 | Butaric et al. |
| 6,629,981 B2 | 10/2003 | Bui et al. |
| 6,645,237 B2 | 11/2003 | Klumb et al. |
| 6,645,238 B1 | 11/2003 | Smith |
| 6,656,212 B2 | 12/2003 | Ravenscroft et al. |
| 6,660,031 B2 | 12/2003 | Tran et al. |
| 6,660,032 B2 | 12/2003 | Klumb et al. |
| 6,663,660 B2 | 12/2003 | Dusbabek et al. |
| 6,666,881 B1 | 12/2003 | Richter et al. |
| 6,669,719 B2 | 12/2003 | Wallace et al. |
| 6,676,666 B2 | 1/2004 | Vrba et al. |
| 6,679,910 B1 | 1/2004 | Granada |
| 6,689,120 B1 | 2/2004 | Gerdts |
| 6,692,521 B2 | 2/2004 | Pinchasik |
| 6,699,274 B2 | 3/2004 | Stinson |
| 6,702,843 B1 | 3/2004 | Brown et al. |
| 6,702,846 B2 | 3/2004 | Mikus et al. |
| 6,709,425 B2 | 3/2004 | Gambale et al. |
| 6,716,238 B2 | 4/2004 | Elliott |
| 6,726,714 B2 | 4/2004 | DiCaprio et al. |
| 6,733,519 B2 | 5/2004 | Lashinski et al. |
| 6,736,839 B2 | 5/2004 | Cummings |
| 6,802,858 B2 | 10/2004 | Gambale et al. |
| 6,814,746 B2 | 11/2004 | Thompson et al. |
| 6,818,014 B2 | 11/2004 | Brown et al. |
| 6,821,291 B2 | 11/2004 | Bolea |
| 6,830,575 B2 | 12/2004 | Stenzel et al. |
| 6,833,002 B2 | 12/2004 | Stack et al. |
| 6,833,003 B2 | 12/2004 | Jones et al. |
| 6,843,802 B1 | 1/2005 | Villalobos et al. |
| 6,858,034 B1 | 2/2005 | Hijlkema et al. |
| 6,860,899 B1 | 3/2005 | Rivelli, Jr. |
| 6,875,212 B2 | 4/2005 | Shaolian et al. |
| 6,936,058 B2 | 8/2005 | Forde et al. |
| 6,936,065 B2 | 8/2005 | Khan et al. |
| 6,989,024 B2 | 1/2006 | Hebert et al. |
| 7,004,964 B2 | 2/2006 | Thompson et al. |
| 7,011,673 B2 | 3/2006 | Fischell et al. |
| 7,074,236 B2 | 7/2006 | Rabkin et al. |
| 7,172,620 B2 | 2/2007 | Gilson |
| 7,300,460 B2 | 11/2007 | Levine et al. |
| 7,393,357 B2 | 7/2008 | Stelter et al. |
| 2001/0034548 A1 | 10/2001 | Vrba et al. |
| 2001/0047185 A1 | 11/2001 | Satz |
| 2001/0049547 A1 | 12/2001 | Moore |
| 2001/0049550 A1 | 12/2001 | Martin et al. |
| 2002/0002397 A1 | 1/2002 | Martin et al. |
| 2002/0032431 A1 | 3/2002 | Kiemeneij |
| 2002/0035393 A1 | 3/2002 | Lashinski et al. |
| 2002/0040236 A1 | 4/2002 | Lau et al. |
| 2002/0045928 A1 | 4/2002 | Boekstegers |
| 2002/0045930 A1 | 4/2002 | Burg et al. |
| 2002/0049490 A1 | 4/2002 | Pollock et al. |
| 2002/0068966 A1 | 6/2002 | Holman et al. |
| 2002/0072729 A1 | 6/2002 | Hoste et al. |
| 2002/0077693 A1 | 6/2002 | Barclay et al. |
| 2002/0095147 A1 | 7/2002 | Shadduck |
| 2002/0095168 A1 | 7/2002 | Griego et al. |
| 2002/0099433 A1 | 7/2002 | Fischell et al. |
| 2002/0120322 A1 | 8/2002 | Thompson et al. |
| 2002/0120323 A1 | 8/2002 | Thompson et al. |
| 2002/0120324 A1 | 8/2002 | Holman et al. |

(56) References Cited

U.S. PATENT DOCUMENTS

| | | |
|---|---|---|
| 2002/0138129 A1 | 9/2002 | Armstrong et al. |
| 2002/0147491 A1 | 10/2002 | Khan et al. |
| 2002/0161342 A1 | 10/2002 | Rivelli et al. |
| 2002/0169494 A1 | 11/2002 | Mertens et al. |
| 2002/0188341 A1 | 12/2002 | Elliott et al. |
| 2003/0014103 A1 | 1/2003 | Inoue |
| 2003/0018319 A1 | 1/2003 | Kiemeneij |
| 2003/0036768 A1 | 2/2003 | Hutchins et al. |
| 2003/0040771 A1 | 2/2003 | Hyodoh et al. |
| 2003/0040772 A1 | 2/2003 | Hyodoh et al. |
| 2003/0055377 A1 | 3/2003 | Sirhan et al. |
| 2003/0065375 A1 | 4/2003 | Eskuri |
| 2003/0069521 A1 | 4/2003 | Reynolds et al. |
| 2003/0105508 A1 | 6/2003 | Johnson et al. |
| 2003/0135266 A1 | 7/2003 | Chew et al. |
| 2003/0149467 A1 | 8/2003 | Linder et al. |
| 2003/0163156 A1 | 8/2003 | Hebert et al. |
| 2003/0163189 A1 | 8/2003 | Thompson et al. |
| 2004/0010265 A1 | 1/2004 | Karpiel |
| 2004/0049547 A1 | 3/2004 | Matthews et al. |
| 2004/0093063 A1 | 5/2004 | Wright et al. |
| 2004/0097917 A1 | 5/2004 | Keane |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0220585 A1 | 11/2004 | Nikolchev |
| 2004/0260377 A1 | 12/2004 | Flomenblit et al. |
| 2005/0049668 A1 | 3/2005 | Jones et al. |
| 2005/0049669 A1 | 3/2005 | Jones et al. |
| 2005/0049670 A1 | 3/2005 | Jones et al. |
| 2005/0080430 A1 | 4/2005 | Wright, Jr. et al. |
| 2005/0096724 A1 | 5/2005 | Stenzel et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0220836 A1 | 10/2005 | Falotico et al. |
| 2005/0246010 A1 | 11/2005 | Alexander et al. |
| 2006/0085057 A1 | 4/2006 | George et al. |
| 2006/0111771 A1 | 5/2006 | Ton et al. |
| 2006/0136037 A1 | 6/2006 | DeBeer et al. |
| 2006/0247661 A1 | 11/2006 | Richards et al. |
| 2006/0270948 A1 | 11/2006 | Viswanathan et al. |
| 2006/0271097 A1 | 11/2006 | Ramzipoor et al. |
| 2006/0276886 A1 | 12/2006 | George et al. |
| 2007/0027522 A1 | 2/2007 | Chang et al. |
| 2007/0043419 A1 | 2/2007 | Nikolchev et al. |
| 2007/0073379 A1 | 3/2007 | Chang et al. |
| 2007/0100414 A1 | 5/2007 | Licata et al. |
| 2007/0100415 A1 | 5/2007 | Licata |
| 2007/0100416 A1 | 5/2007 | Licata |
| 2007/0100418 A1 | 5/2007 | Licata |
| 2008/0015541 A1 | 1/2008 | Rosenbluth et al. |
| 2008/0071309 A1 | 3/2008 | Mazzocchi et al. |
| 2008/0221666 A1 | 9/2008 | Licata et al. |

FOREIGN PATENT DOCUMENTS

| | | |
|---|---|---|
| EP | 0 747 021 | 12/1996 |
| EP | 1 157 673 | 11/2001 |
| EP | 1 518 515 | 3/2005 |
| JP | 2002-538938 | 11/2002 |
| WO | WO 97/12563 | 4/1997 |
| WO | WO 97/48343 | 12/1997 |
| WO | WO 98/23241 | 6/1998 |
| WO | WO 99/04728 | 2/1999 |
| WO | WO 99/08740 | 2/1999 |
| WO | WO 00/18330 | 4/2000 |
| WO | WO 00/56248 | 9/2000 |
| WO | WO 01/78627 | 10/2001 |
| WO | WO 03/073963 | 9/2003 |
| WO | WO 2004/087006 A2 | 10/2004 |
| WO | WO 2005/092241 | 10/2005 |
| WO | WO 2005/094727 | 10/2005 |

OTHER PUBLICATIONS

Kandzari et al., "Clinical and Angiographic Efficacy of a Self-Expanding Nitinol Stent in Saphenous Vein Graft Atherosclerotic Disease" Am. Heart J 145(5):868-874 (2003).
Rieu et al., "Radical Force of Coronary Stents: A Comparative Analysis" Catherization and Cardiovascular Interventions 46:380-391 (1999).
Schuessler et al., Stent Materials and Manufacturing: Requirements and Possibilities/Opportunities, ASM Materials & Processes, Anaheim, CA (Sep. 8-10, 2003).
Stoeckel et al., "A Survery of Stent Desings" Min Invas Ther & Allied Technol 11(4):137-147 (2002).
Welt et al., "Coronary Artery Stents: Design and Biologic Considerations" Cardiology Special Edition 9(2) 9-14 (2003).
Rogers, C, "DES Overview: Agents: release mechanism and stent platform".
Bonsignore, Craig, "A Decade of Evolution in Stent Design" Cordis Corporation Nitinol Devices & Components. 47533 Westinghouse Drive, Fremont. California 94539.
Fischell, M.D. Facc, Tim A.. "A Fixed Guidewire Stent Delivery System Rationale and Design" TCT. Washington, D.C. (Sep. 24. 2002).
Poncet, Philippe P., "Nitinol Medical Device Design Considerations" MEMRY Corporation. 4065 Campbell Avenue, Menlo Park. California 94025. pp. 1-12.
Definitions of "abut" and "wire"—Random House College Dictionary, 1980, New York, 7 and 510.
International Search Report and Written Opinion of PCT Application No. PCT/US2006/034311, mailed Mar. 22, 2007, 7 pages total.
International Search Report of PCT Application No. PCT/US2006/34130, mailed Nov. 23, 2007, 8 pages total.
International Preliminary Report on Patentability of PCT Application No. PCT/US2006/34130, dated Oct. 14, 2008, 8 pages total.
International Search Report and Written Opinion of PCT Application No. PCT/US2004/008909, mailed Sep. 24, 2004, 6 pages total.
Office Action of Japanese Application No. 2006-507500, mailed Nov. 18, 2009, 9 pages (including English Translation).
Examination Report of Singaporean Application No. 2005050976-1, mailed Feb. 28, 2007, 10 pages total.
Written Opinion of Singaporean Application No. 2005050976-1, mailed Apr. 27, 2006, 9 pages total.
Examination Report of Australian Application No. 2004226464, mailed Jul. 17, 2007, 2 pages total.
Partial Supplementary European Search Report of EP Application No. 04758233, mailed Jun. 6, 2007, 5 pages total.
Supplementary European Search Report of EP Application No. 04758233, mailed Nov. 7, 2007, 7 pages total.
Communication from the Examining Division for of EP Application No. 04758233, mailed Aug. 29, 2008, 5 pages total.
Communication from the Examining Division of EP Application No. 06802753.1, mailed Mar. 18, 2009, 1 page total.
Supplementary European Search Report of EP Application No. 06802753.1, mailed Dec. 4, 2008, 9 pages total.

* cited by examiner

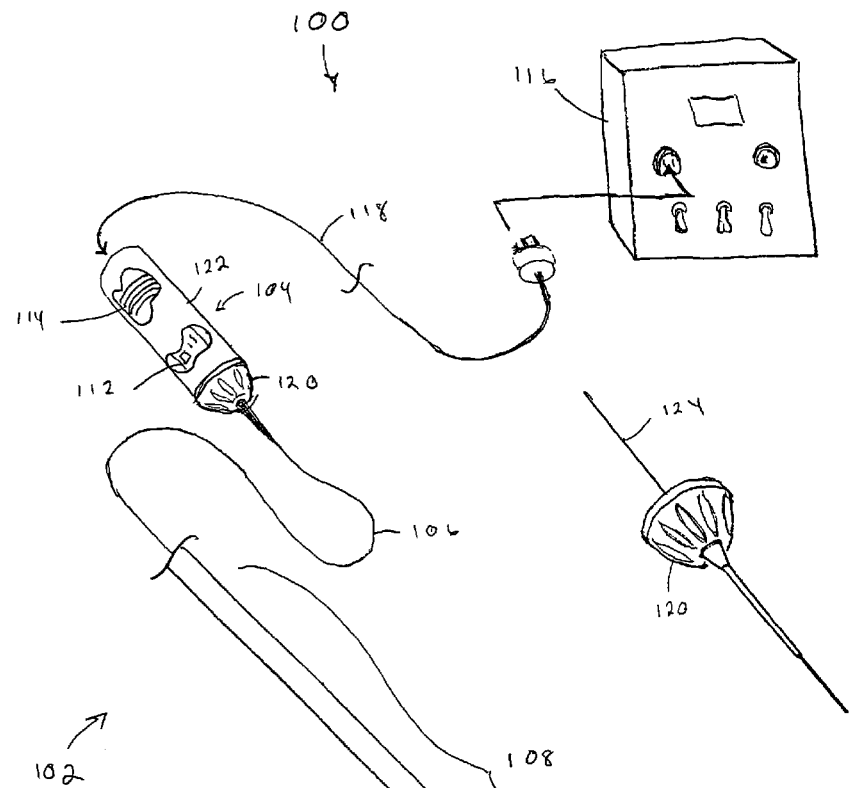
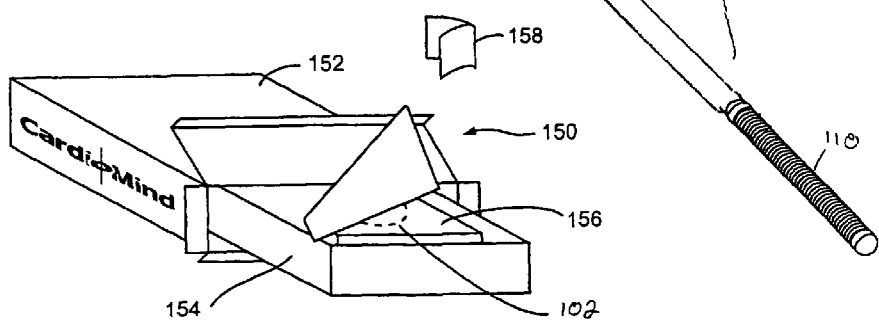
Fig. 5

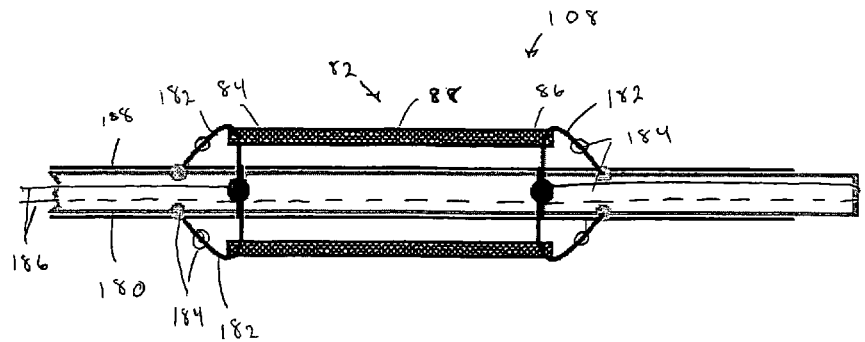
Fig. 7A
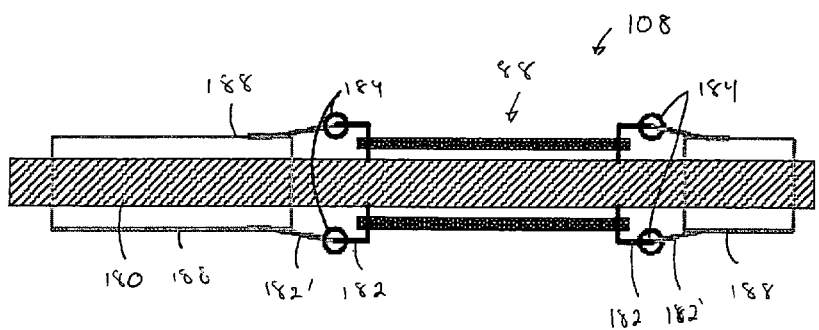
Fig. 7B
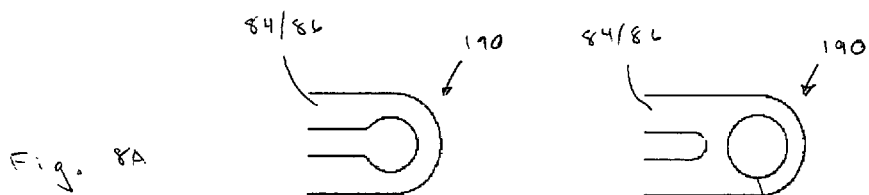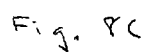
Fig. 8A    Fig. 8C
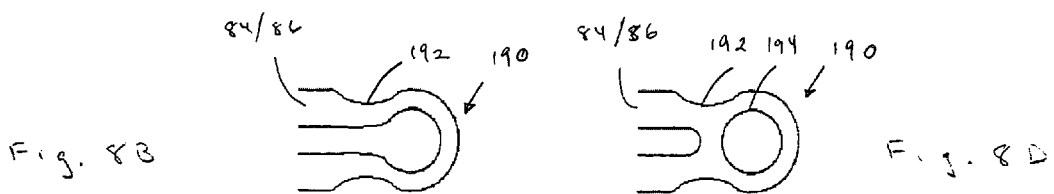
Fig. 8B    Fig. 8D

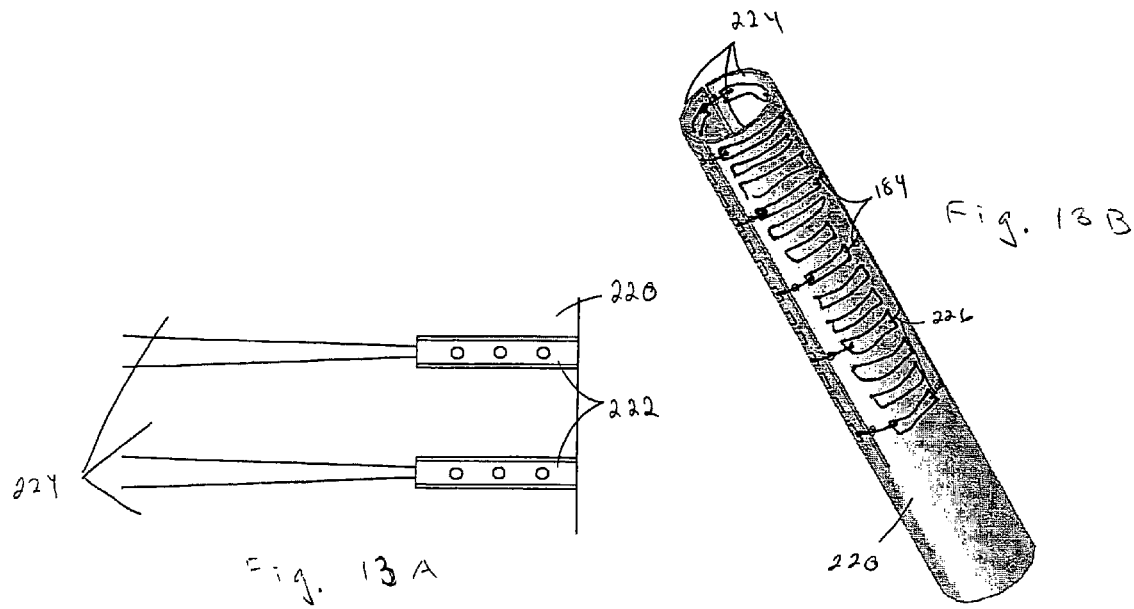
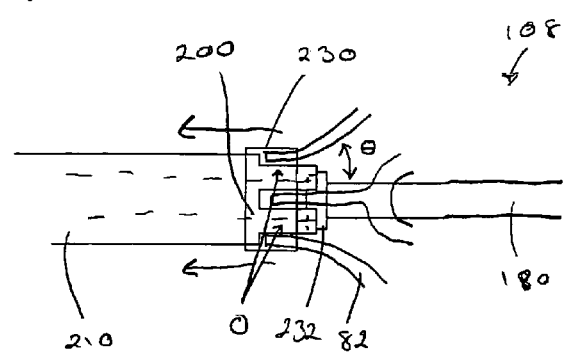
Fig. 14
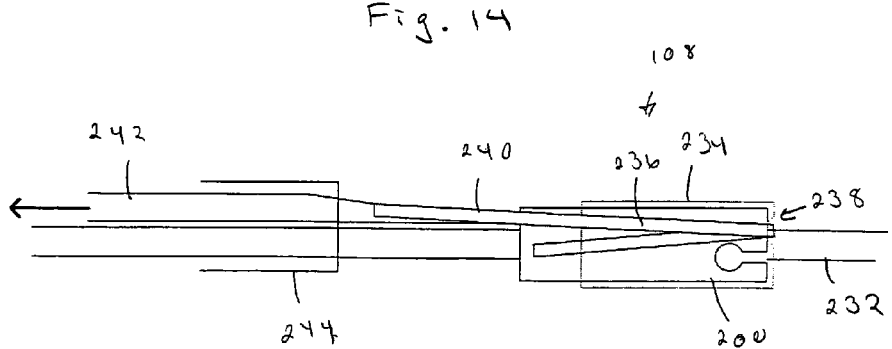
Fig. 15

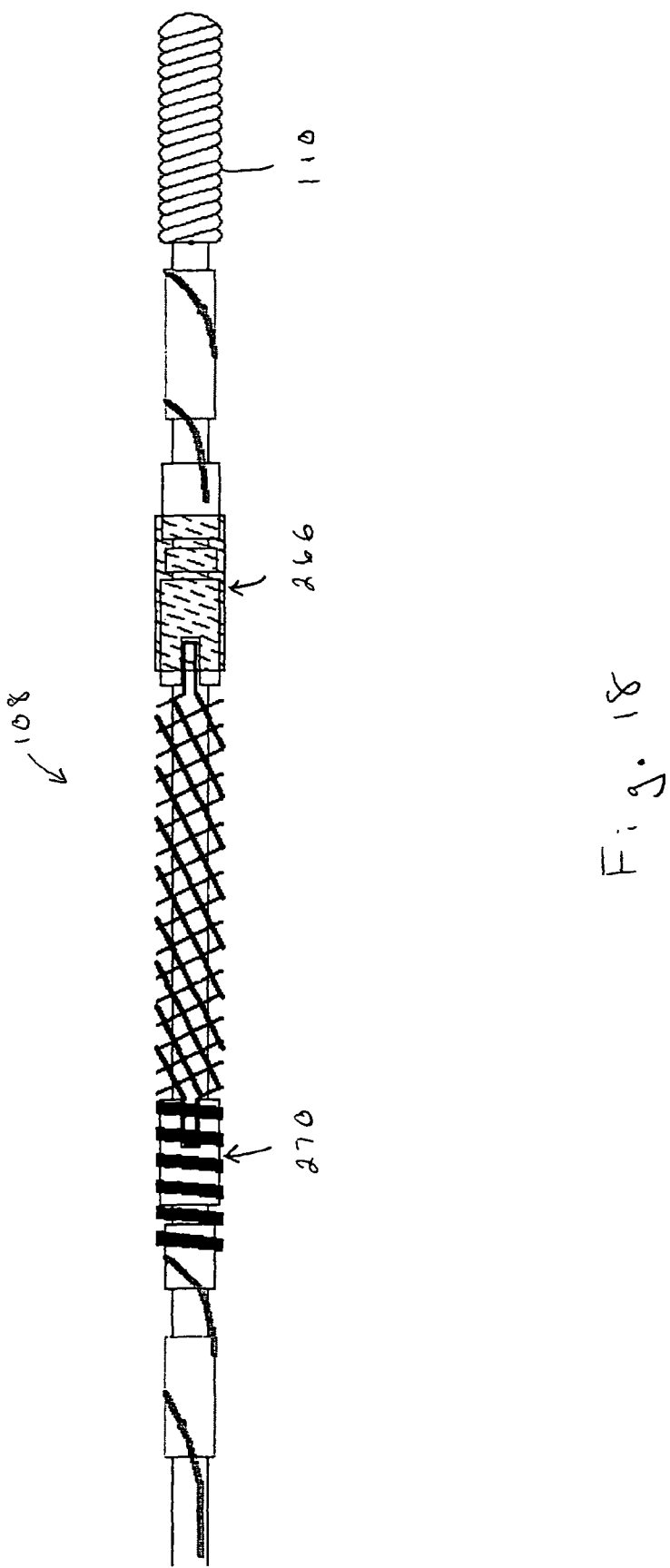

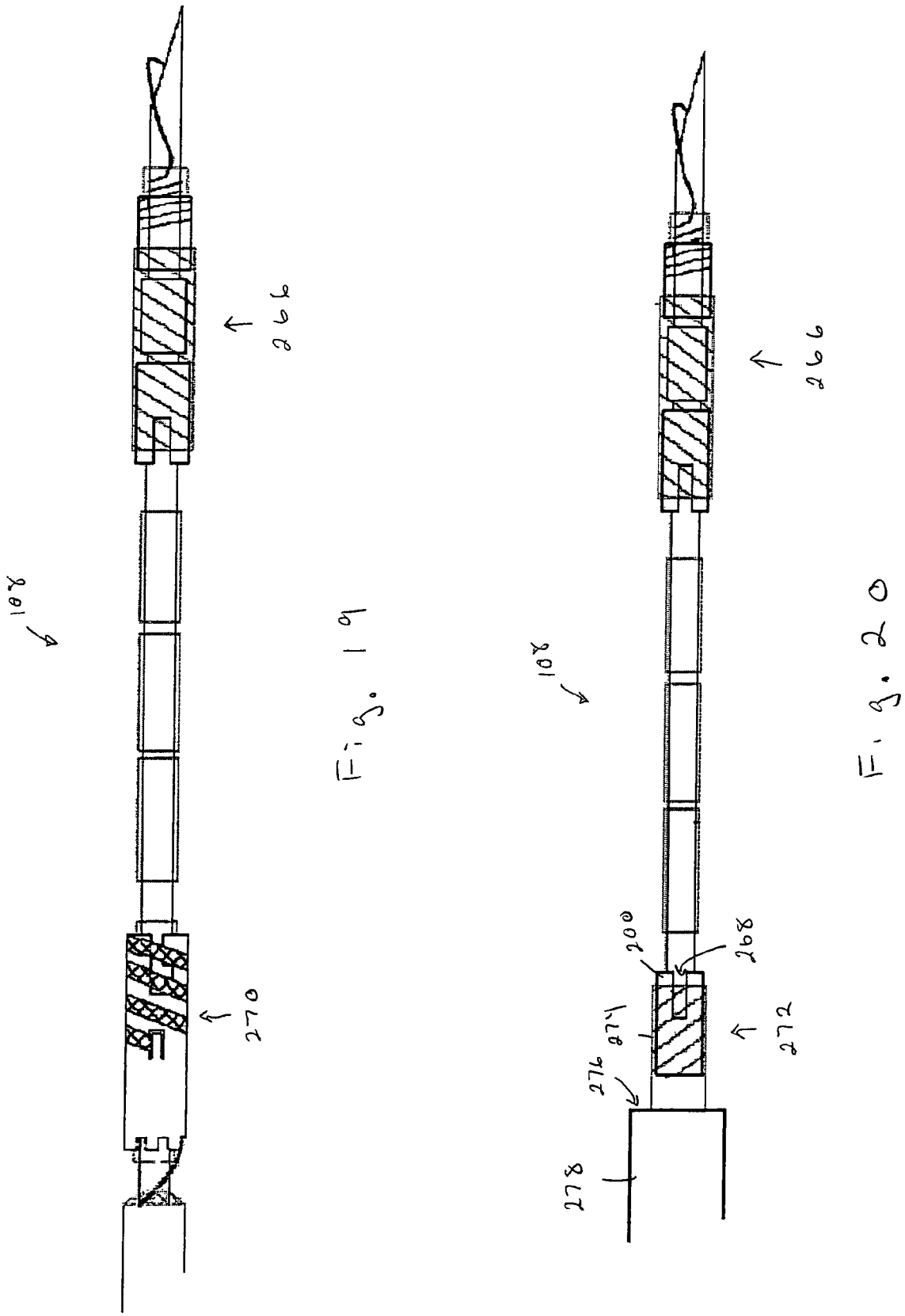

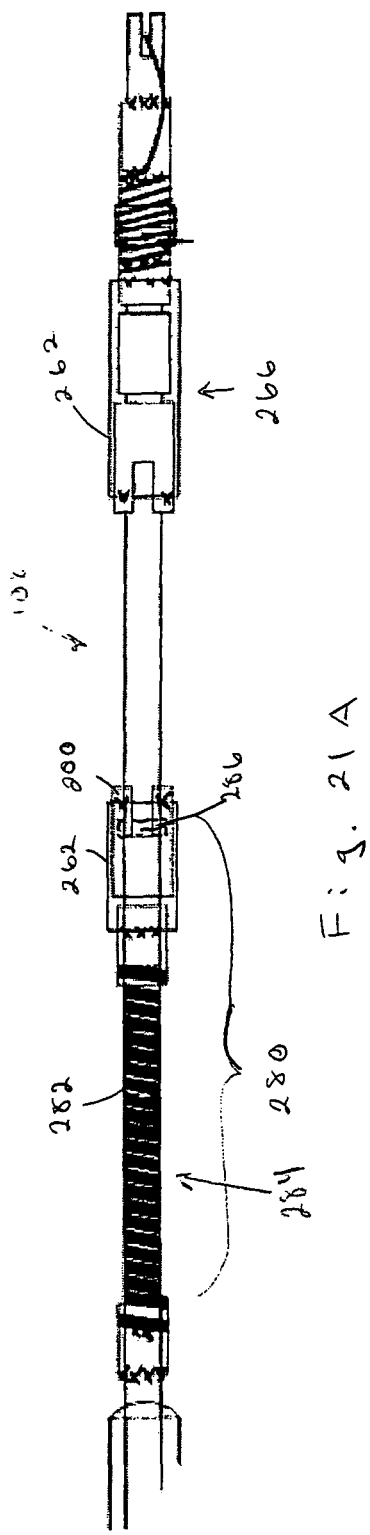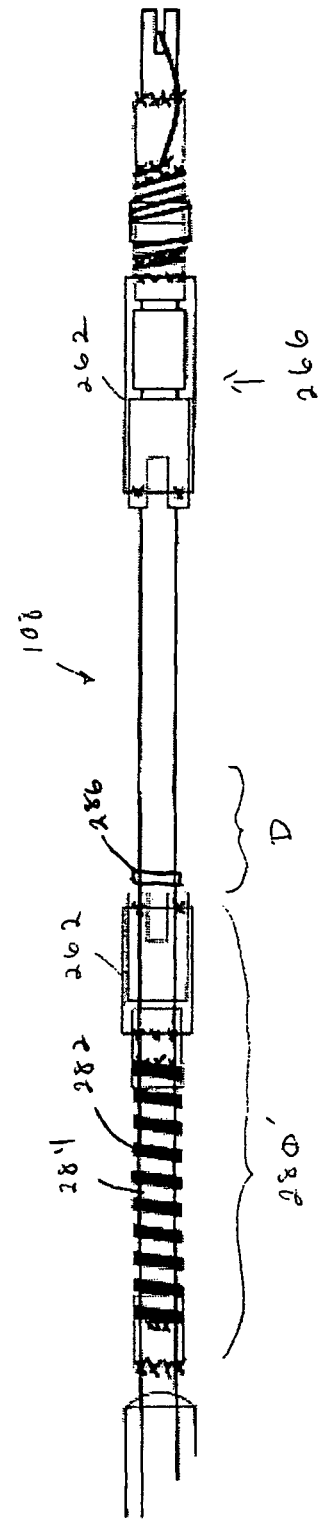

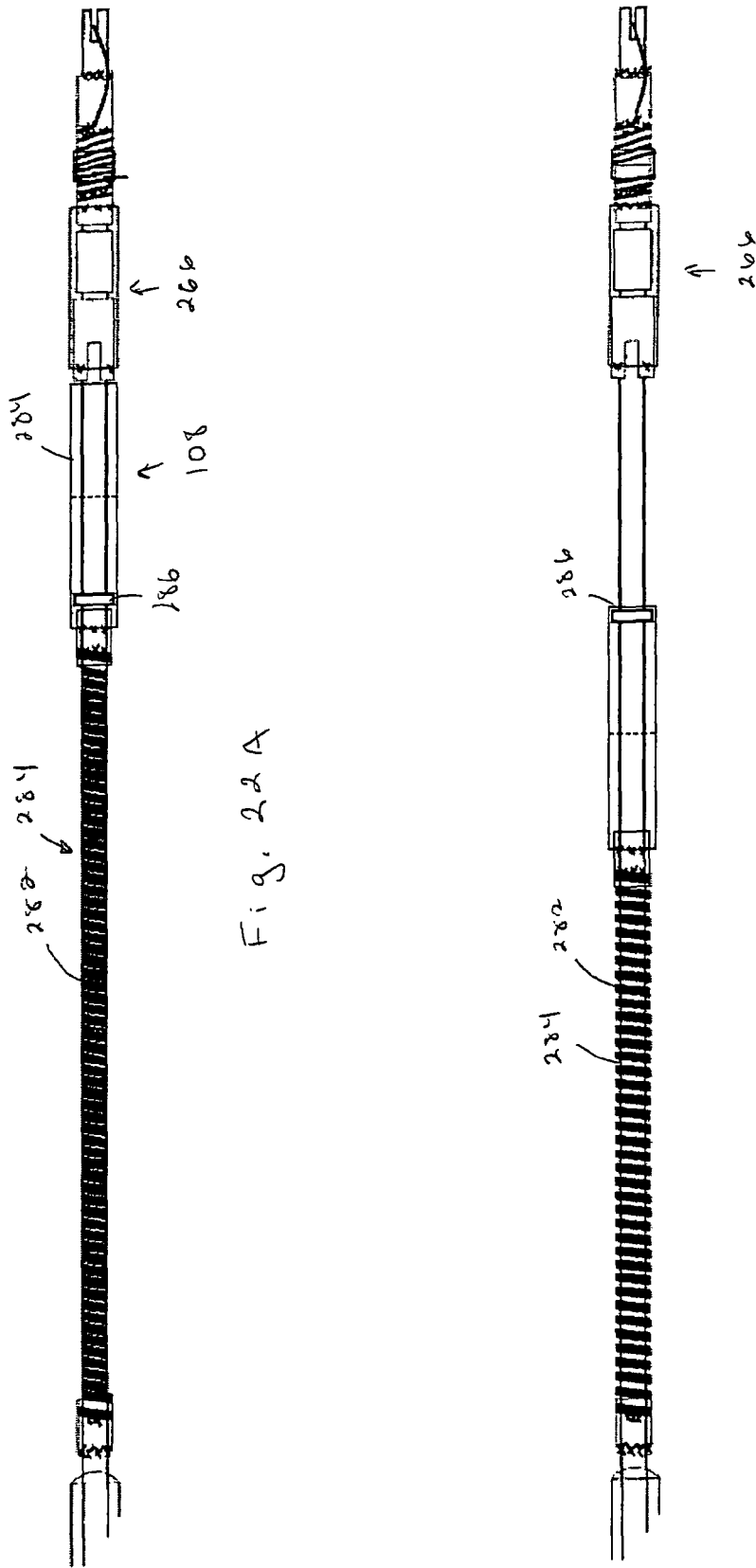

UNTWISTING RESTRAINT IMPLANT DELIVERY SYSTEM

BACKGROUND

Implants such as stents and occlusive coils have been used in patients for a wide variety of reasons. One of the most common "stenting" procedures is carried out in connection with the treatment of atherosclerosis, a disease which results in a narrowing and stenosis of body lumens, such as the coronary arteries. At the site of the narrowing (i.e., the site of a lesion) a balloon is typically dilatated in an angioplasty procedure to open the vessel. A stent is set in apposition to the interior surface of the lumen in order to help maintain an open passageway. This result may be effected by means of a scaffolding support alone or by virtue of the presence of one or more drugs carried by the stent to aide in the prevention of restenosis.

Various stent designs have been developed and used clinically, but self-expandable and balloon-expandable stent systems and their related deployment techniques are now predominant. Examples of self-expandable stents currently in use are the Magic WALLSTENT® stents and Radius stents (Boston Scientific). A commonly used balloon-expandable stent is the Cypher® stent (Cordis Corporation). Additional self-expanding stent background is presented in: "An Overview of Superelastic Stent Design," Min. Invas Ther & Allied Technol 2002: 9(3/4) 235-246, "A Survey of Stent Designs," Min. Invas Ther & Allied Technol 2002: 11(4) 137-147, and "Coronary Artery Stents: Design and Biologic Considerations," Cardiology Special Edition, 2003: 9(2) 9-14, "Clinical and Angiographic Efficacy of a Self-Expanding Stent" AM Heart J 2003: 145(5) 868-874.

Because self-expanding prosthetic devices need not be set over a balloon (as are balloon-expandable designs), self-expanding stent delivery systems can be designed to a relatively smaller outer diameter than their balloon-expandable counterparts. As such, self-expanding stents may be better suited to reach the smallest vasculature or to achieve access in more difficult cases.

One consideration pertinent to the delivery of self-expanding stent designs concerns frictional forces internal to the subject delivery system. Internal forces can be a significant issue with respect to system actuation. Testing by the assignee hereof has clearly demonstrated a loss of motive force available to actuate a distally located restraint when the delivery system is subject to conditions of or simulating tortuous anatomy. As such, systems that require little or no direct user actuation of components to effect stent release are desirable. Examples of such systems are presented in a number of patents.

U.S. Pat. No. 5,873,907 offers a system employing circumferential bands, each having an electrolytically erodable section, where the bands hold a stent in a collapsed configuration until the sections' joints are released. U.S. Pat. No. 5,980,514 discloses a system in which a self-expanding stent is held onto a wire directly by electrolytically erodable joints. U.S. Pat. No. 6,716,238 describes a system in which one or more tethers are connected to a stent to releasably restrain it for delivery or to stabilize its position during delivery. The tethers may work in conjunction with a sheath to hold a distal end of the stent, allowing withdrawal of the sheath from the stent to effect release. When the sheath is withdrawn, the stent expands radially, but is not fully released until the connections between the tethers and the stent are mechanically broken, electrolytically eroded or melted away. In another embodiment described in the '238 patent, one or more tethers is wrapped around the body of the stent to tie it down until released.

Upon closer examination, each of the referenced systems has serious limitations—either in terms of clinical practicality, basic mechanical feasibility or both. Issues variously presented by the referenced stent delivery systems include:

1) risk of tissue damage or vulnerable plaque dislodgement by drawing released tethers or bands past/between an open/opening stent and a vessel wall;
2) inability to employ drug elution matrix upon a stent because of direct connection of an erodable solder joint to the stent;
3) unpredictability of joint or release segment corrosion;
4) long deployment times as a result of large amounts of material to erode to effect implant release; and/or
5) bulkiness in system design.

Other issues may be presented as well as appreciated by those with skill in the art. Accordingly, to maximize the potential benefits of electrolytic release for stents and/or other implants, there exists a need for improved systems.

SUMMARY

Variations of the invention hold a radially-expandable, implantable prosthesis (such as a stent) in a collapsed configuration for delivery with the assistance of one or more members including an electrolytically erodable or disintegratable section. Unlike most electrolytic-based implant delivery systems, none of those in the subject invention employ a "joint" that joins or attaches the implant directly to the delivery member. Neither do the electrolytically erodible sections secure tethers or bands restraining the central diameter of the implant body.

Rather, either a twist imparted to the implant or a tubular sleeve holds the implant in a compressed profile. The sacrificial electrolytic member maintains the implant or restraining sleeve in a preloaded configuration until release. Upon release, the implant is freed to untwist or the sleeve withdrawn therefrom. In each case, the implant is then able to expand.

One aspect of the invention offers systems in which one or more ends of an implant or prosthesis such as a stent are held in a highly stable manner by a clinically and mechanically robust, yet compact holding/restraining and releasing means. In these variations of the invention, one portion of the means comprises pass-through or male-female interlocking features between an end of the implant and a delivery guide member body. The engaging features associated with the delivery member body may comprise as few as two features; more preferably, three, four or more features arranged around a ring. Most advantageously, the multiple members are symmetrically spaced apart.

The implants employed in connection with the present invention are often stents. Most typically, the stents employed are lattice, cage or successive linked ring-type structures. Often they are cut from tubing or they are mesh-like woven or assembled bodies. However, other means or modes of manufacture are possible as well.

In a number of variations of the invention, the configuration of the stent or other implant employed is critical to the operation of the system. In these systems, foreshortening of the implant (i.e., decreasing length of the body, or at least a portion thereof, in transitioning from a collapsed to an expanded state) plays an important roll in stent release. In those examples of the invention where foreshortening plays a role in implant release, the implant is often adapted to be twisted and it is this twisting that assists in holding the stent at a desired diameter.

In order to hold such an implant in a radially compressed and twisted state, the implant (e.g., a stent) optionally includes one or more extensions or projections from its main body. Such extensions are adapted to nest or otherwise interface with complimentary seat features set upon or retained by the guide body portion of the implant delivery system. The projections may simply comprise elongate members that offer a laterally stable interface or comprise hook-shaped forms (e.g., "J", "T", "L", "S", "V" etc. shapes) that also an axially stable interface. Alternatively, the implant body or projections therefrom may instead incorporate or define openings or receptacle features. As such, the prosthesis or the delivery guide seat features may extend partially to a certain depth (i.e., forming a pocket). Alternatively, the openings may extend through the entire member.

Stated broadly, either the implant and/or the delivery guide may include male and/or female interlocking features. A grasping form of interface may be employed to axially tension the implant and/or provide secure capture at one side of the implant to provide "bail-out" potential. The delivery guide side of the interface may be referred to as a "seat" or otherwise. Especially, where the members hook into one another, they may be regarded as "nesting" features. "Lock" and "key" terminology may also be used to describe the features.

Alternatively, the implant/delivery guide interface may be adapted for sliding receipt and release. Such configurations enable various self or automatic release approaches. For these, extension from the implant or even the crowns of adjacent stent struts may provide the interface with delivery guide component(s). For these types of interfaces, "key" and "way" terminology may be most appropriate. Still, the delivery device side may be regarded as a "seat" or "seating" region or portion.

In any of these systems employing a stent that is both radially compressed and twisted, various approaches to loading the implant onto or into the delivery guide may be employed. One highly advantageous method that forms an aspect of the present invention involves pre-loading the implant into a sleeve. The stent is compressed by hand, with an automated "crimper" such as produced by Machine Solutions, Inc., or otherwise, without a substantial twist and loaded into a tubular body close in diameter to its final size upon or in the delivery guide. By "close" in diameter, what is meant is that it is within at least 33%, or more preferably about 25%, or even about 10% of its final diameter. Then, with the stent so-constrained, it is twisted from either or both ends before or after partial or full attachment to the delivery guide.

The sleeve may comprise a plurality of separate pieces or segments (most conveniently two or three). As such, the individual segments can be rotated relative to one another to assist in twisting the stent. In addition, axial manipulation of the relation of thin individual segments can be employed to allow the implant to bulge outwardly over one section. The foreshortening caused by this action may then allow positioning and then axially loading end interface members by manipulating the segments to collapse the bulging.

As for the electrolytically releasable retention members, one class comprises wire or ribbon passing through at least one portion of the implant (including any extension or projection therefrom). A loop of material threaded through a receptacle or adjacent one or more crown portions of a stent offers a very strong, yet simple connection to the delivery guide. The loop may itself be erodable at a section, or an erodable bridging segment may be incorporated in the loop. An even more elegant connection employs a pin, post or rivet-like member received through the implant. The pin or rivet structure may be headed (i.e., have a bulbous or flattened head or mushroom-like shape) in order to prevent lift-off of the implant member. Erosion of the head and/or periphery of the structure will then release the implant.

Systems employing these pass-through type of securing features may work alone by holding an implant such as a stent in a twisted state. Alternatively, they may hold such an implant in a twisted and/or axially stretched configuration with a retractable tubular sheath or restraint sleeve over the implant. In this way, the electrolytically released components can partially restrain the implant so as to reduce sleeve holddown and/or withdrawal forces. The pinned/threaded connections are particularly space-efficient and, thus, suited for use with supplemental restraining device components while maintaining small device crossing profiles.

When employed with a retaining sleeve, as few as one location on the implant can be secured by the electrolytically released component(s). For a stent, the location may be proximal or distal. A distal location may offer improved sleeve withdrawal characteristics; a proximal location may simplify electrical conduction and or performance issues. Employing both proximal and distal electrolytic retainer attachment locations enable axial and/or torque-based implant diameter reduction techniques to reduce the force required for restraint withdrawal.

Another class of retainers or retaining and release means or releaseable means comprises an overriding means or covering including at least one electrolytically erodable section that releasably secures ends of an implant in association with a seating portion or portions of a delivery guide. In one variation, the means comprises a-wrap or band or plurality of bands. Upon release of one or more sections, the band opens or wrap loosens. In another variation, the radial retention member comprises a sleeve or casing with one or more electrolytically erodable sections that allow (or upon release, cause) the structure to open. Such a "flower petal" type design may be soldered or welded together in a pre-stressed state in order that it self expands upon eroding connecting webbing, solder, weld point(s), etc.

When either one of such structures is opened or relaxed, the captured projections of the implant can release from complimentary delivery guide side features. When the projection(s) and seat(s) offer a keyed interface, those on the implant can lift or be pushed out of plane to release at least one portion of the implant. When the projection(s) and seat(s) are adapted for sliding receipt and release, the latter will occur more readily upon release of the wrap or band and force holding parts together (if only by virtue of static friction).

As with the above variation of the invention in which retention members pass through one or more portions of the implant, those retention members that overlay one or more portions of the implant may secure the proximal and/or distal side the implant or point(s) between. They may be used in complimentary pairs or with other structures as is convenient. In the latter example, either one of the wrap-around or openable sleeve retainer may be set at the distal end of the stent with a mechanical release mechanism positioned at the proximal side of the stent. Examples of such mechanically-actuated systems including retractable mini-sheaths and wire or suture cut-down bands are presented in U.S. patent application Ser. No. 11/266,587, entitled, "Twist-Down Implant Delivery Technologies" filed on Nov. 2, 2005, which application is incorporated herein by reference in its entirety.

Furthermore, different ones of electrolytically releasable means may be set at opposite ends (or simply different locations) of the implant. Certain advantageous pairings are elaborated upon below, especially for stent release. For the sake of discussion here, however, one such combination employs the "flower petal" style means at the proximal side of the device and wrap-around means at the distal end. After implant delivery, a proximal-side open "flower petal" device will easily collapse when withdrawn into a delivery catheter. On the distal side, however, the open structure could get caught. In contrast, a loose filament released from a wrap-around means can easily be drawn into the delivery catheter regardless of location on the delivery guide. Yet, because the flower petal approach may be more easily slipped over the stent in a final loading step than a filament wound around the stent and secured, the former structure may be desired on at least one side of the system for ease of assembly. Of course, other exemplary systems employing the various retention and release means are possible in which the rationale for the combinations may be apparent upon further review of the subject specification.

Equally applicable to a mix-and-match approach are electrolytically releasable means that are specifically adapted to permit an implant's release by its mating portion(s) sliding out of a restraining configuration upon some triggering action. In other words, either one or both sides of a stent delivery system according to the present invention may employ this type of release approach.

As for the various device configurations that enable such action, a first one is advantageously used to initiate release of the implant. In one example, the releasable retention means comprises a covered interface held by an electrolytic latch. Once released, the interface rotates—allowing the stent to untwist and expand. The expansion causes the length of the stent to shorten because of its cell or strut geometry. As it shortens (foreshortens) the stent draws itself (e.g., end projections) out of the retaining interface. In one variation, the covering comprises a band. In another example, it comprises a wrap that loosens as the stent unwinds. Such a configuration will allow release of keyed projections, with or without substantial implant foreshortening.

In any case, all of the above-described release members are to be actuated by electrolytic erosion through application of voltage by user action (or computer programming) with a suitable power supply. Other variations of the present invention employ a second implant retaining and release means that is tripped or actuated by action of the first release means or by the resulting configuration of the implant. In these variations of the invention, the second or subsequent means automatically completes implant release. Such action may be desired as a matter of convenience in reducing user activity, it may offer improved release speed or reliability, or it may be desirable for yet one or more other reasons.

Of these auto-release systems, a first type is one in which a floating or non-secured tubular member is set over one end of the implant. Expansion of the implant—as in the example of a stent—drives the tube off of the stent in the direction of expansion. So-displaced, the adjacent captured end of the stent is released. An interlocking key or slip-type interface may be freed-up by virtue of moving the outer sleeve. In either example, the stent may lie upon a core member along its entire length or a region under the projections may be relieved or undercut. Such relief allows for steepening of the angle that the end of the implant can assume without flexing of material. This effect offers improved mechanical advantage for moving the outer sleeve.

Another example of an automatically releasable retention means employs a coil spring attached to or integrally formed with a sleeve. The sleeve is offered, again, to cap the implant member and the delivery guide interface features (i.e., the projection and seat members). Withdrawal of the sleeve permits release. The spring positively locks the sleeve in place in one state and actively withdraws it in a second state. In the locked state, the spring is tightly wound about the system body so that its position is bound-up by frictional forces. In the second state, the spring is opened by untwisting so as to be able to retract freely.

This unwinding of the spring is accomplished by releasing the pre-twist imparted to the adjoining implant. Until released, the spring is held twisted by the twisted implant interfacing with keys or ridge features underlying the sleeve.

When the twisted implant (be it a stent or another medical device) is released, the spring also untwists and is freed from its cinched-down configuration—thereby allowing its retraction from a stretched-out/preloaded state.

As an alternative to the twist-lock approach described above, a spring member (in the form of a coil or otherwise configured) in an axially preloaded state can be secured by an anchor member. The anchor member may comprise an electrolytic latch. Alternatively, an "anchor" line in the form of a ribbon, suture, etc. can be set under the implant and held in place by its radial compression derived from the twist-down. When the twist to the implant is released and the body expands, so-too is the pressure securing the anchor line.

In another variation of the invention, no active release means is employed at a second side of the implant. Rather, the second end of an implant is held by an interface that can be released by simply withdrawing or advancing the delivery system. An advantageous configuration in this regard employs a covered slide-out implant/delivery guide interface at a proximal end of a stent. After distal release of the stent and expansion into contact with the body lumen, the delivery system is withdrawn from the stent, releasing the proximal end. In yet another approach where the proximal side of the delivery system includes the slide-out enabled architecture, an end of a catheter in receipt of the delivery guide is employed to abut the stent proximal/near side. Then advancement of the catheter or withdrawal of the delivery guide further into the catheter releases the near side of the stent.

In a manner related to the spring-back variations of the invention for releasing interface features on one side of a twisted-down implant, the concept can be applied to withdrawal of a sheath or a restraint covering at least a portion of the body of an implant. Specifically, an electrolytic latch can be employed for restraining a stretched-out spring element to withdraw a sheath from up to the entire length of a stent. In one example, the releasable trigger member is connected to a spring member that is only axially stretched. In another variation, the spring member is both axially stretched and twisted. The twisting in this case would be for binding-up the spring or at least assisting in its restraint. Upon release, the restraint untwists and is able to fully retract. When a twisted spring is employed, the implant to be delivered will rotate with the restraint as the restraint is withdrawn. In either of these approaches, end-capture features for the restraint/sheath may resemble or be identical to features described above in connection with releasably securing the end of an implant (i.e., the keyed projection and seat features).

As stated above, the inventive features may be used to deliver any of a variety of implants besides lattice or cage-type stents. Though stents are focused on in this regard, other examples of implants which may be employed with the subject invention include coil stents, embolic protection filters and other "clot-pulling" devices, embolic coils and even application to other technologies. However, in order to function properly in connection with certain variation of the invention, the implants must sometimes be configured such that at least a portion foreshortens during deployment. Still, other ones of the system variations—such as spring-back sheath variations discussed directly above—may work with any sort of deliverable medical device for permanent or temporary implantation. It is also contemplated that those improvements described herein pertaining to methodology, power profiles for electrolytic actuation, insulation and electrical architectures may be applied in delivery systems for any type of implant.

Regarding methodology, the subject methods may include each of the mechanical activities associated with implant release as well as electrical activity. As such, methodology implicit to the use of the devices described forms part of the invention. Such methodology may include that associated with completing an angioplasty, bridging an aneurysm, deploying radially-expandable anchors for pacing leads or an embolic filter, or placement of a prosthesis within neurovasculature, an organ selected from the kidney and liver, within reproductive anatomy such as selected vasdeferens and fallopian tubes or other applications. In some methods, the various acts of implant release are considered; in others, the power profiles, monitoring of power and other aspects of power control are considered.

More particularly, a number of methods according to the present invention involve the manner in which the delivery system operates in releasing an implant. In one such method in which the implant is restrained at two sides, a first side is released by an electrolytic latch, followed by automatic release of the second side, wherein the automatic action is initiated by release of the first side. In another method, two independently releasable ends are released one after the other. This action is accomplished not by the contemporaneous erosion of an electrolytic member on each side of the implant (with staged release controlled by different amounts of material to erode as is known, and suitable for certain variations of the invention disclosed herein) but, rather, by selecting and eroding material incorporated in separate electrical circuits. Yet another delivery method is contemplated in which an electrolytic component is released only on one side of the implant. Such action may be followed by a mechanical release action such as withdrawing or tearing a sheath member manually or activating a "muscle wire" to do the same. Another approach may involve withdrawing or advancing the delivery guide to effect final implant release from a second, slidably releasable means holding the other end of the implant.

Another aspect of the invention provides methods involving power profiles for electrolytic element erosion and hardware/systems and software to control the methods. While electrocoagulation (e.g., by thrombus formation in blood by blood cell attraction to a positive charge) can be a positive factor in embolic coil delivery, it has been appreciated that such action can severely hamper or interfere delivery of other types of implants. Rather than isolating the member to be eroded, however, an aspect of the present invention involves use of power profiles to ameliorate or eliminate any problems with electrocoagulation. Specifically, an AC signal is employed. Not to be bound by the theory, but it is believed that the negative charge of the cycle repulses blood cells. However, to effect the desired erosion, a net positive charge is required. Thus, a positive DC offset is applied to the AC voltage. The positive offset and amplitude of the AC signal yields higher peak voltages to drive electrolytic corrosion. Irrespective of electrocoagulation, these higher peak energies may result in increased erosion and consequent implant deployment. Numerous potential power profiles according to this general principle are detailed below. Furthermore, experimental results are provided which illustrate the effectiveness of such an approach.

Another approach according to the present invention involves system insulation in order to focus erosion, or at least maximize current density at the point of erosion. Generally, it is known that "fast acting" detachable systems can be produced by insulating or electrically isolating everything but that portion of the system where electrolytic erosion is desired. The present invention improves upon this concept in certain variations by producing system components with high-strength titanium or titanium alloy. In addition, they can be anodized to form an oxide layer insulative to DC voltage. The components are typically pre-anodized. Yet, when using higher voltages, the systems are "self-healing" such that any scratches, etc. exposing material to unintended corrosion/erosion will skin-over and maintain their integrity. Such a system is highly advantageous as it eliminates the need for polymeric insulation; further, such a system need not rely on the use of noble (or high Mendelev number) metal material selection to protect components that can be costly or cumbersome to apply, or cause failures if disturbed.

Yet another aspect of the invention concerns the electrical architecture or design of the subject systems. In order to minimize or eliminate any potential risk associated with the electrical signal carried by the system, certain variations of the invention are configured such that the release member(s) are positively charged at the point where erosion is desired and the section(s) are directly adjacent (i.e., within about 1 cm, preferably less) to a negatively charged element. In one variation of the invention, the subject retention and release means is located at a distal end of the delivery system. It is electrically connected to the (net) positive side of a power source via wiring running within a delivery guide body made from hypotubing.

In all, the implant retention member configurations, electrical connectivity and conductivity as well as the manner in which they are employed can vary in a number of ways according to the present invention. Furthermore, some variations of the invention are adapted to release an implant or prosthesis such as a stent without the use of any mechanically actuated components. In other variations of the invention, systems may include manually-actuated or activated components. However, it is envisioned that the former class of purely electrically-actuated systems may offer particular flexibility as subcomponents for systems requiring off-axis implant delivery.

Used as a subcomponent, a discrete electrically-actuated system as described in detail below could be attached in a non-axial or "V" shaped configuration to allow treating a crossing vessel in a "T" shaped site such as at or near the basilar artery junction. In which case, a tether underlying the implant or a distal sheath may be provided to re-constrain an open "V" configuration to allow its recapture and withdrawal into a catheter body. Alternatively, an electrically-actuated system could be provided at a distal end of a system that includes a drawstring or wire to force a dramatic prolapse in the system in order to treat such a vessel configuration as described above. Unless such features are provided, however, the subject systems typically comprise flexible linear or uni-directional delivery guide members without extensions, arms or fittings at the far end of the delivery guide body.

The delivery systems described herein offer a number of advantages in their efficient construction and ability to deliver implants with or without coatings in highly challenging applications. Those with skill in the art may appreciate further benefits or advantages of the subject inventive variations.

Definitions

The term "stent" as used herein includes any stent, such as coronary artery stents, other vascular prosthesis, or other radially expanding or expandable prosthesis or scaffold-type implant suitable for the noted treatments or otherwise. Exemplary structures include wire mesh or lattice patterns and coils, though others may be employed in certain variations of the present invention. A "self-expanding" stent as used herein is a scaffold-type structure (serving any of a number of purposes) that expands from a reduced-diameter (be it circular or otherwise) configuration to an increased-diameter configuration. The mechanism for shape recover may be elastic or pseudoelastic. While it is generally desirable to employ an alloy (such as nickel-titanium, or Nitinol alloy) set for use as a superelastic alloy, it may alternatively employ thermal shape memory properties to drive expansion upon release.

A "wire" as used herein generally comprises a common metallic member such as made of stainless steel or another material. The wire may be at least partially coated or covered by a polymeric material (e.g., with an insulating polymer such as Polyamide, or a lubricious material such as TEFLON®, i.e., PolyTetraFluoroEthelyne or PTFE). Still further, the "wire" may be a hybrid structure with metal and a polymeric material (e.g., Vectran™, Spectra™, Nylon, etc.) or composite material (e.g., carbon fiber in a polymer matrix). The wire may be in the form of a filament, bundle of filaments, cable, ribbon or in some other form. It is generally not hollow. The wire may comprise-different segments of material along an overall length.

A "hypotube" or "hypotubing" as referred to herein means small diameter tubing in the size range discussed below, generally with a thin wall. The hypotube may specifically be hypodermic needle tubing. Alternatively, it maybe wound or braided cable tubing, such as provided by Asahi Intec Co., Ltd. or otherwise. As with the "wire" discussed above, the material defining the hypotube may be metallic, polymeric or a hybrid of metallic and polymeric or composite material.

An "atraumatic tip" may comprise a plurality of spring coils attached to a tapered wire section. At a distal end of the coils typically terminate with a bulb or ball that is often made of solder. In such a construction, the coils and/or solder are often platinum alloy or another radiopaque material. The coils may also be platinum, or be of another material. In the present invention, the wire section to which the coils are attached may be tapered, but need not be tapered. In addition, alternate structures are possible. In one example, the atraumatic tip may comprise a molded tantalum-loaded 35 durometer Pebax™ tip. However constructed, the atraumatic tip may be straight or curved, the latter configuration possibly assisting in directing or steering the delivery guide to a desired intravascular location.

To "connect" or to have or make a "connection" between parts refers to fusing, bonding, welding (by resistance, by pressure, laser, chemically, ultrasonically, etc.), gluing, pinning, crimping, clamping or otherwise mechanically or physically joining, attaching or holding components together (permanently or temporarily). To "electrically connect" or to have or make an "electrical connection" between parts refers to providing a low-resistance path for current to flow upon the application of a voltage (AC and/or DC). The connection may be in the form of a wire, a trace of material such as cladding or plating overlying a selected area, conductive fill material (such as silver-loaded epoxy resin), adhesive, solder, etc.

BRIEF DESCRIPTIONS OF THE DRAWINGS

The figures provided herein are not necessarily drawn to scale, with some components and features being exaggerated for clarity. Each of the figures diagrammatically illustrates aspects of the invention. Of these:

FIG. 5 shows an overview of a delivery system according to the present invention;

FIGS. 7A and 7B show wrap-through restraint delivery guide variations;

FIGS. 8A-8D show stent end variations that may be used in conjunction with the delivery guides of FIGS. 7A and 7B;

Figure 12A:
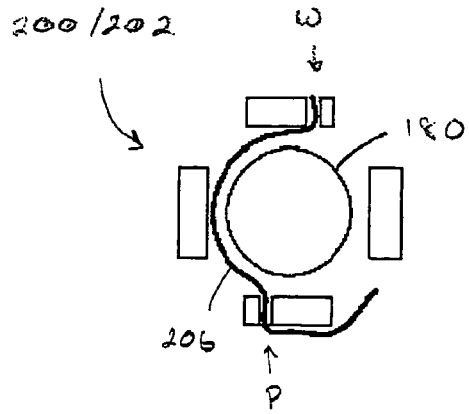
Figure 12B:
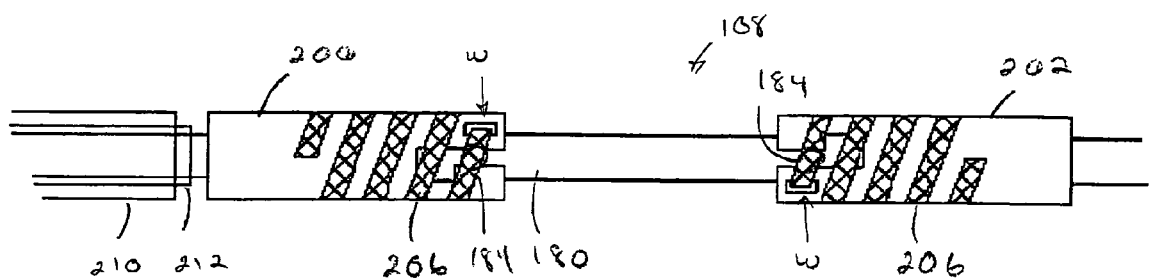
Figure 12C:
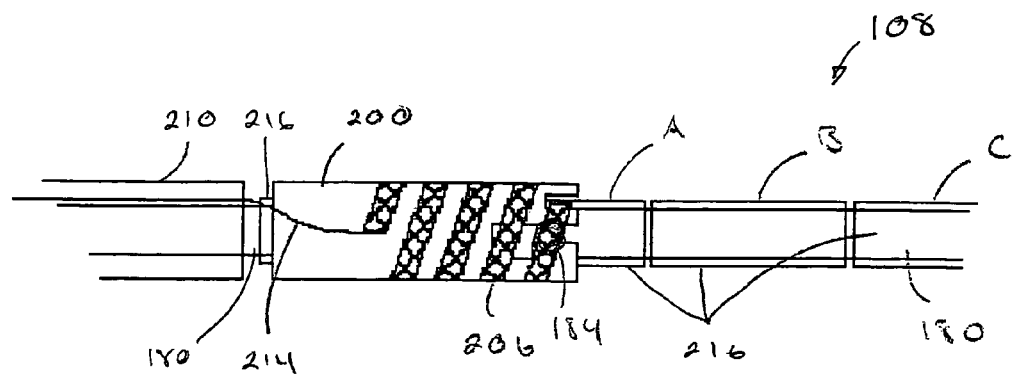
Figure 16:
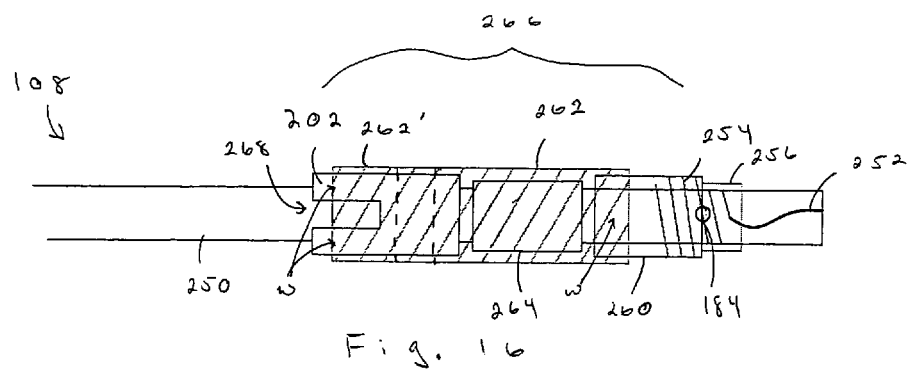
Figure 17A:
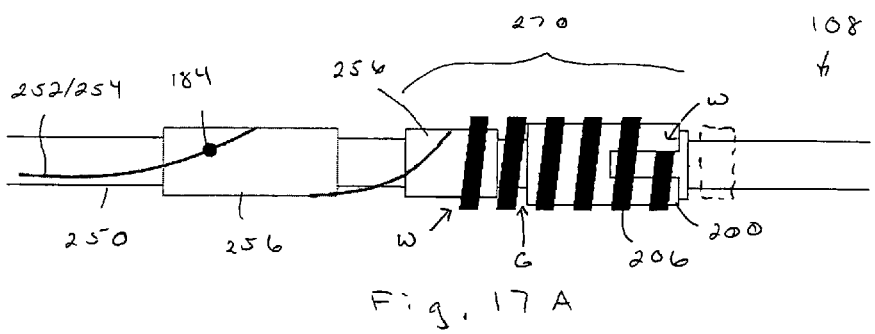
Figure 17B:
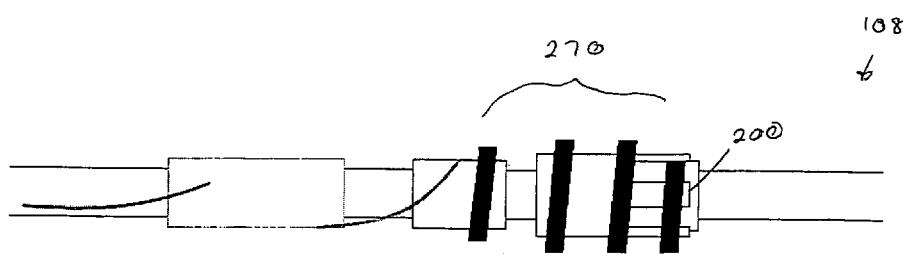
Figure 23:
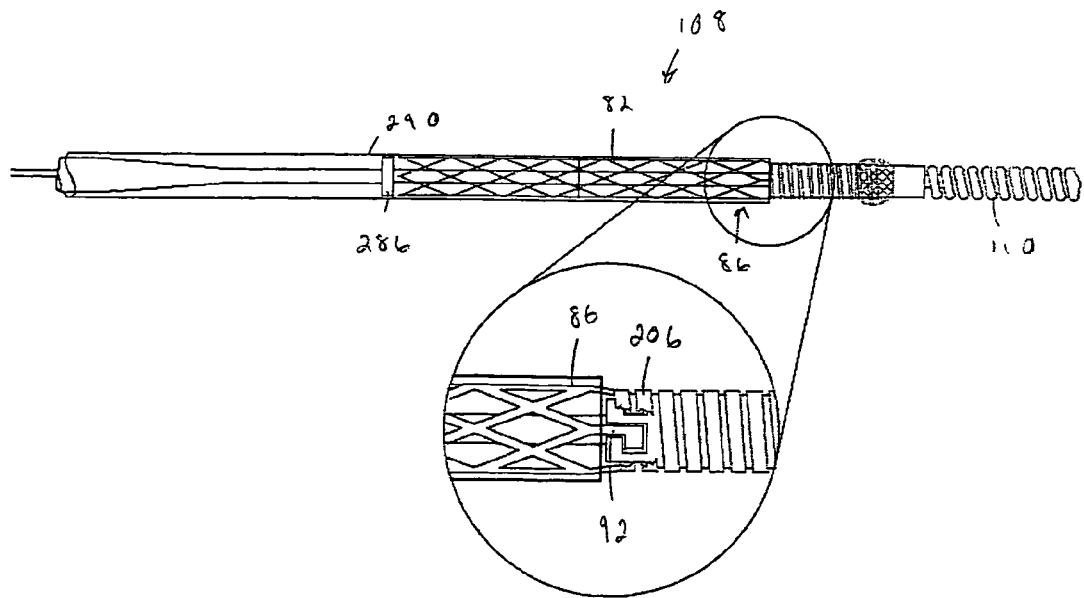
Figure 24A:
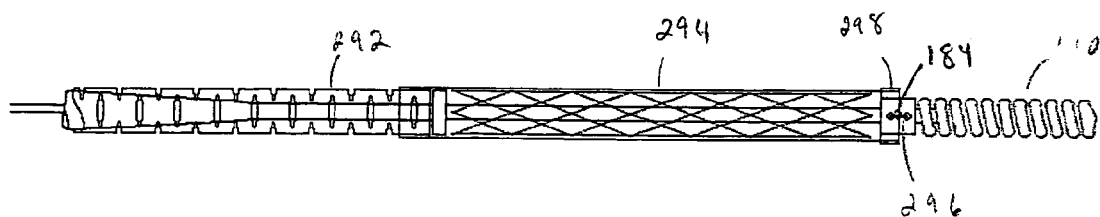
Figure 24B:
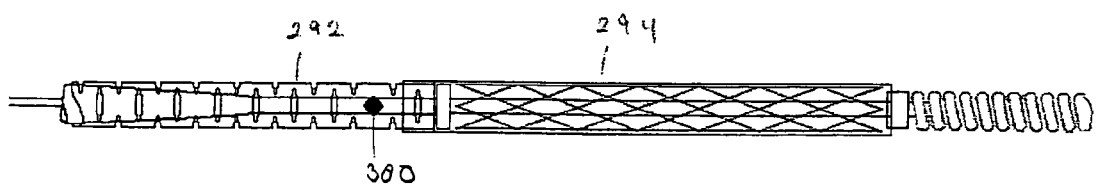
Figure 25:
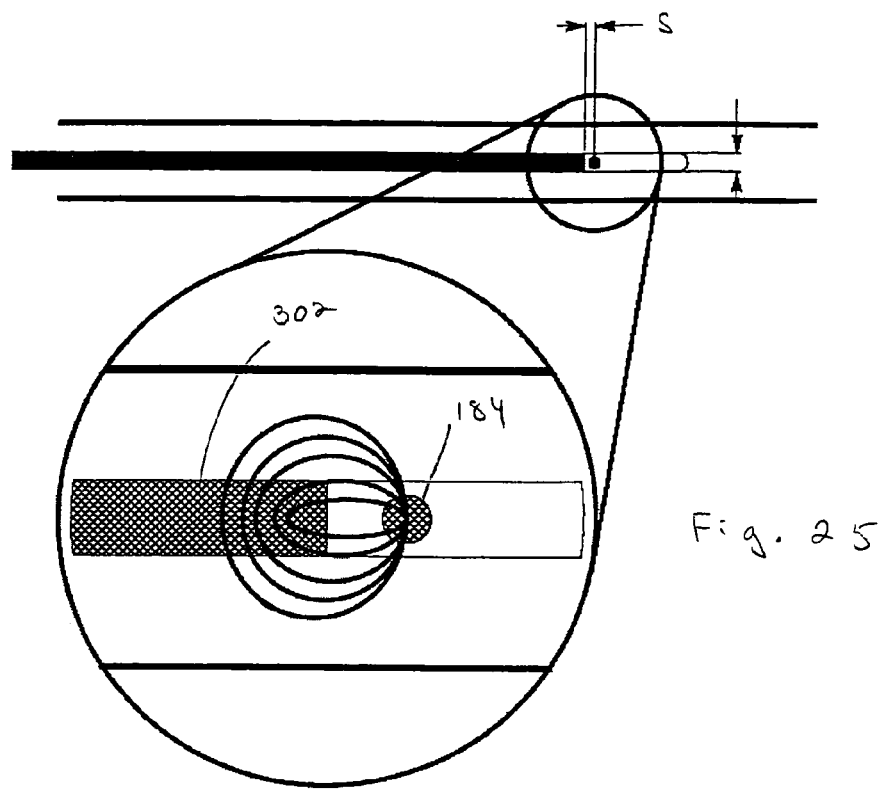
Figure 26:
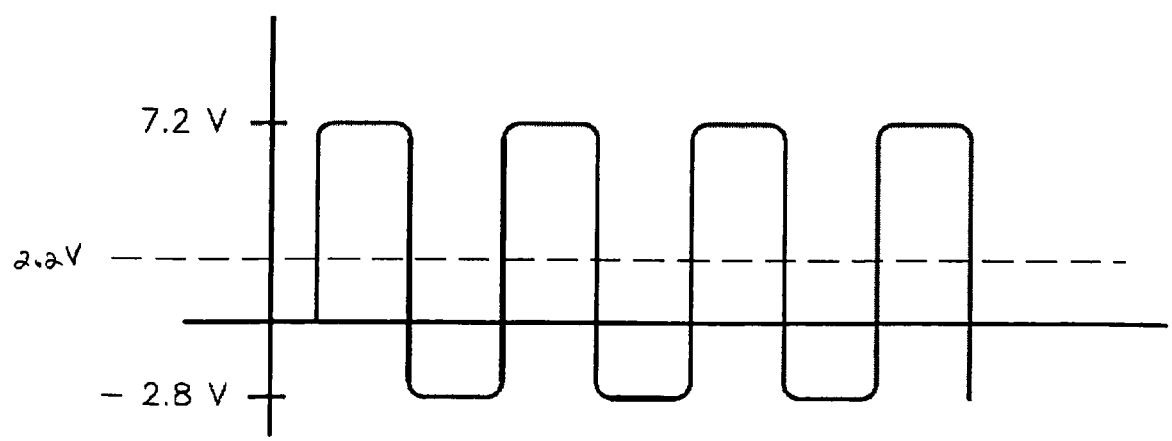

FIG. 12A shows an end sectional view of a manner in which to construct a wrap-over electrolytically releasable ember to cover an end of an implant to restrain it for delivery; FIG. 12B shows the wrap-over variation of FIG. 12A upon a delivery guide in which the stent is absent for the sake of clarity in illustrating features; FIG. 12C show a variations of a near side of such a delivery guide as shown in FIG. 12B, illustrating a different electrical connection approach;

FIG. 13A shows an alternate stent end cover variation including electrolytically separable segments; FIG. 13B shows a related construction in which wire segments are provided to hold and release the cover segments;

FIG. 14 shows a portion of a delivery guide with a slidable cover releasing the ends of an implant;

FIG. 15 shows a portion of a delivery guide with a teardown cover for holding and releasing the ends of an implant;

FIG. 16 shows a portion of a delivery guide with a rotatable covered member for holding and releasing the ends of an implant;

FIGS. 17A and 17B show a portion of a delivery guide with a rotatable and expandable ribbon cover for holding and releasing the ends of an implant, respectively;

FIG. 18 shows a distal portion of a delivery guide variation employing features as shown in FIGS. 16 and 17A and 17B, with a stent loaded thereon and a distal atraumatic tip;

FIG. 19 shows a distal portion of a delivery guide variation with features as shown in FIGS. 13A and 16, minus an implant and distal tip;

FIG. 20 shows a distal portion of yet another delivery guide variation employing features as shown in FIG. 16 for implant release at a distal end and a basic slotted interface at a proximal side, together with a catheter body as may be used to assist proximal implant release;

FIGS. 21A and 21B show two states of a distal portion of a delivery guide in which features shown in FIG. 16 provide for distal implant release and a self locking/auto-releasing member provides for proximal implant release;

FIGS. 22A and 22B show two states of a distal portion of a delivery system resembling that in FIGS. 21A and 21 B, where the auto-releasing member effects withdrawal of a restraint covering at least a portion of a body of an implant;

FIG. 23 shows a delivery guide variation employing a tubular restraint for releasing a stent secured by distal keyed and covered electrolytically releasable implant/delivery guide interface;

FIGS. 24A and 24B shown preloaded spring-back restraint systems secured in position by an electrolytic latch and joint, respectively, until release;

FIG. 25 illustrates principles behind an e-safe electrolytic corrosion based delivery system;

FIG. 26 shows an exemplary power profile for driving indirect-release electrolytic implant delivery systems according the present invention or other systems as may be employed by a medical practitioner.

Variation of the invention from the embodiments pictured is, of course, contemplated.

DETAILED DESCRIPTION OF THE INVENTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Self-Expanding Stent Designs and Opportunities

Figure 1:
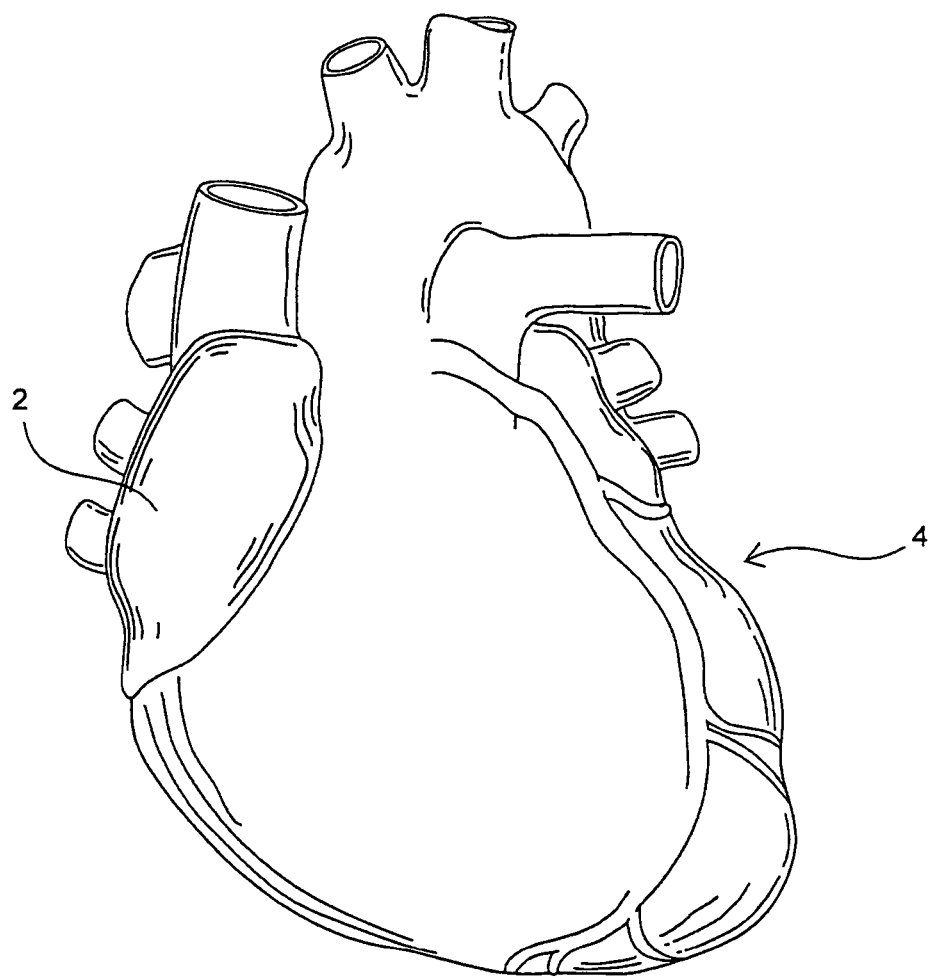
FIG. 1 shows a heart in which its vessels may be the subject of one or more angioplasty and stenting procedures.

In light of this framework, FIG. 1 shows a heart 2 in which its vessels may be the subject of one or more angioplasty and/or stenting procedures. To date, however, significant difficulty or impossibility is confronted in reaching smaller coronary arteries 4. If a stent and a delivery system could be provided for accessing such small vessels and other difficult anatomy, an additional 20 to 25% of percutaneous coronary procedures could be performed with such a system. Such potential offers opportunity for huge gains in human healthcare and a concomitant market opportunity—with the further benefit of avoiding loss of income and productivity of those treated.

Features of the present invention are uniquely suited for a system able to reach small vessels (though use of the subject systems s not limited to such a setting.) By "small" coronary vessels, it is meant vessels having an inside diameter from between about 1.5 to 2 mm and up to about 3 mm in diameter. These vessels include, but are not limited to, the Posterior Descending Artery (PDA), Obtuse Marginal (OM) and small diagonals. Conditions such as diffuse stenosis and diabetes produce situations that represent other access and delivery challenges that can be addressed with a delivery system according to the present invention. Other extended treatment areas addressable with the subject systems include vessel bifurcations, chronic total occlusions (CTOs), and prevention procedures (such as in stenting of vulnerable plaque).

It may be preferred to use a drug eluting stent (DES) in such an application to aid in preventing restenosis. A review of suitable drug coatings and available vendors is presented in "DES Overview: Agents, release mechanism, and stent platform" a presentation by Campbell Rogers, MD incorporated by reference in its entirety. However, bare-metal stents may be employed in the present invention.

Examples of various therapeutic agents that may be used in or on the subject prosthesis include, but are not limited to, antibiotics, anticoagulants, antifungal agents, anti-inflammatory agents, antineoplastic agents, antithrombotic agents, endothelialization promoting agents, free radical scavengers, immunosuppressive agents, antiproliferative agents, thrombolytic agents, and any combination thereof. The therapeutic agent may be coated onto the implant, mixed with a biodegradable polymer or other suitable temporary carrier and then coated onto the implant, or, when the implant is made from a polymeric material dispersed throughout the polymer. The agent can be directly applied to the stent surface(s), or introduced into pockets or an appropriate matrix set over at least an outer portion of the stent.

While some might argue that the particular role and optimal usage of self expanding stents has yet to be defined, they offer an inherent advantage over balloon expandable stents. The latter type of devices produce "skid mark" trauma (at least when delivered uncovered upon a balloon) and are associated with a higher risk of end dissection or barotraumas caused at least in part by high balloon pressures and related forces when deforming a balloon-expandable stent for deployment to account for recoil upon balloon deflation.

Yet, with an appropriate deployment system, self-expanding stents may offer one or more of the following advantages over balloon-expandable models: 1) greater accessibility to distal, tortuous and small vessel anatomy—by virtue of decreasing crossing diameter and increasing compliance relative to a system requiring a deployment balloon, 2) sequentially controlled or "gentle" device deployment, 3) use with low pressure balloon pre-dilatation (if desirable) to reduce barotraumas, 4) strut thickness reduction in some cases reducing the amount of "foreign body" material in a vessel or other body conduit, 5) opportunity to treat neurovasculature—due to smaller crossing diameters and/or gentle delivery options, 6) the ability to easily scale-up a successful treatment system to treat larger vessels or vice versa, 7) a decrease in system complexity, offering potential advantages both in terms of reliability and system cost, 8) reducing intimal hyperplasia, and 9) conforming to tapering anatomy—without imparting complimentary geometry to the stent (though this option exists as well).

Figure 2A:
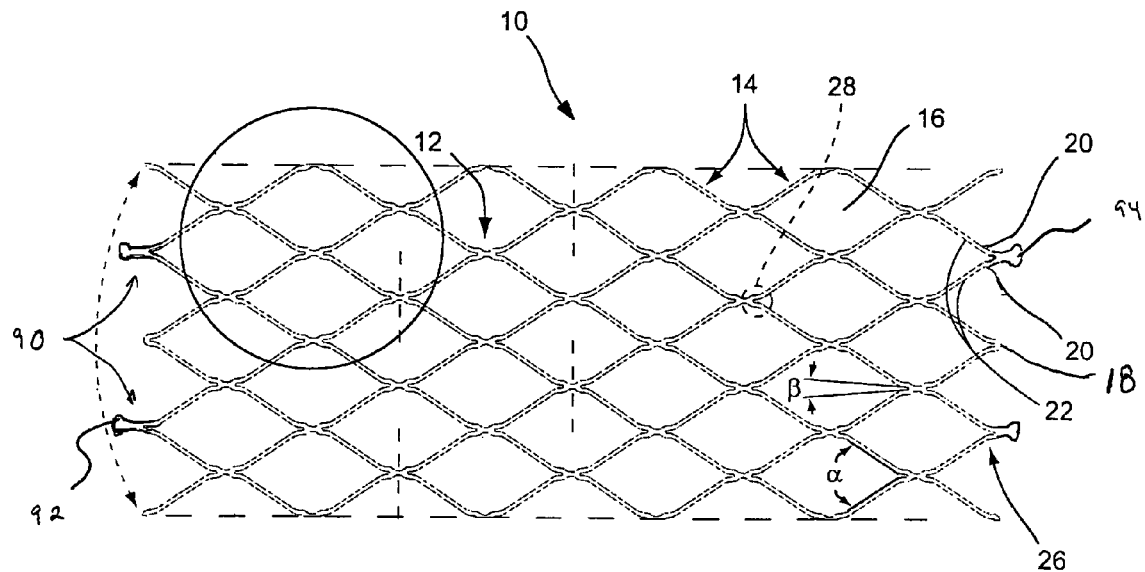
FIGS. 2A and 2B show a first expanded stent cut pattern and an expanded view of a section of the same, respectively.

At least some of these noted advantages may be realized using a stent 10 as shown in FIG. 2A. The stent pattern pictured is well suited for use in small vessels. It may be collapsed to an outer diameter of about 0.018 inch (0.46 mm), or even smaller to about 0.014 inch (0.36 mm)—including the restraint/joint used to hold it down—and expanded to a size (fully unrestrained) between about 1.5 mm (0.059 inch) or 2 mm (0.079 inch) or 3 mm (0.12 inch) and about 3.5 mm (0.14 inch).

In use, the stent will be sized so that it is not fully expanded when fully deployed against the wall of a vessel in order to provide a measure of radial force thereto (i.e., the stent will be "oversized" as discussed above). The force will secure the stent and offer potential benefits in reducing intimal hyperplasia and vessel collapse or even pinning dissected tissue in apposition.

Stent 10 preferably comprises NiTi that is superelastic at or below room temperature (i.e., as in having an Af as low as 15 degrees C. or even 0 degrees C.). Also, the stent is preferably electropolished to improve biocompatibility and corrosion and fatigue resistance. The stent may be a DES unit as referenced above. The stent may be coated with gold and/or platinum to provide improved radiopacity for viewing under medical imaging. It may be biodegradable.

For a stent able to collapse to an outer diameter of about 0.012 inches and expand to about 3.5 mm, the thickness of the NiTi is about 0.0025 inch (0.64 mm). Such a stent is designed for use in a 3 mm vessel or other body conduit, thereby providing the desired radial force in the manner noted above. Further information regarding radial force parameters in coronary stents may be noted in the article, "Radial Force of Coronary Stents: A Comparative Analysis," Catheterization and Cardiovascular Interventions 46: 380-391 (1999), incorporated by reference herein in its entirety.

In one manner of production, the stent in FIG. 2A is laser or EDM cut from round NiTi tubing, with the flattened-out pattern shown wrapping around the tube as indicated by dashed lines. In such a procedure, the stent is preferably cut in its fully-expanded shape. By initially producing the stent to full size, the approach allows cutting finer details in comparison to simply cutting a smaller tube with slits and then heat-expanding/annealing it into its final (working) diameter. Avoiding post-cutting heat forming also reduces production cost as well as the above-reference effects.

Figure 2B:
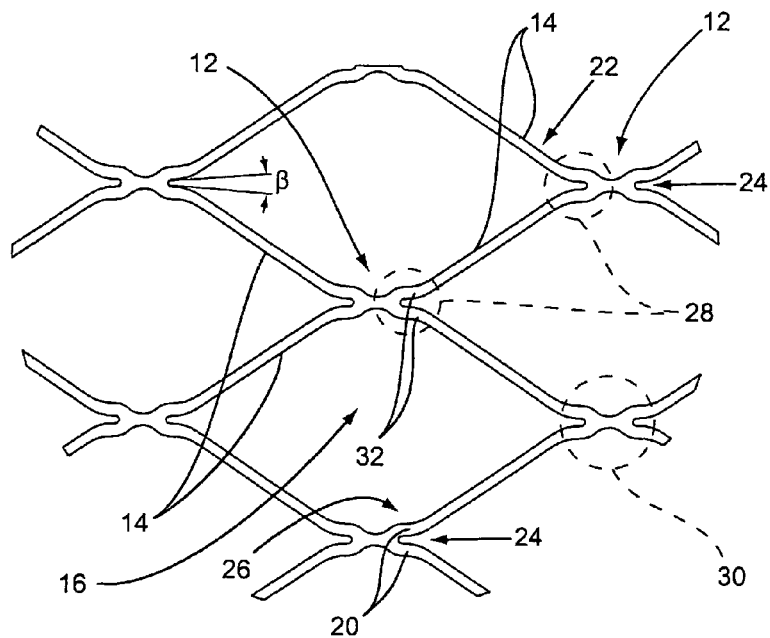

Regarding the finer details of the subject stent, as readily observed in the detail view provided in FIG. 2B, necked down bridge sections 12 are provided between axially/horizontally adjacent struts or arms/legs 14, wherein the struts define a lattice of closed cells 16. Such a closed cell designs facilitate twist-down of the stent where applicable because the otherwise free ends of an open ended cell (or successive ring) design have a tendency to radially lift-off in a radial direction due to complex stress distributions.

In certain variations of the invention, however, the bridge sections can be strategically separated or opened as indicated by the broken lines in FIG. 2A. Doing so disrupts the closed cell pattern discussed above, but may increase stent conformability to tortuous anatomy. One situation in which such modification may be useful is in those variations of the invention employing a sleeve or sheath overlying the stent. In any case, to facilitate such tuning of the stent, the bridge sections are preferably sufficiently long so that fully rounded ends may be formed internally to the lattice just as shown at terminal ends or crowns 18 of the cells not carrying stent/delivery system interface features.

As for the optional double-concave profile of each strut bridge 12 shown, this form is advantageous in that it reduces material width (relative to what would otherwise be presented by a parallel side profile) to improve flexibility and thus trackability and conformability of the stent within the subject anatomy while still maintaining the option for separating/breaking the cells apart. Whether cut to provide rounded end portions or adjoined by a bridge section 12, strut junction sections 28 connect circumferentially or vertically adjacent struts (as illustrated). Where no bridge sections are provided, the junction sections can be unified between horizontally adjacent stent struts as indicated in region 30.

Further optional features of stent 10 are employed in the strut junction sections 28 of the design. Specifically, strut ends 20 increase in width relative to medial strut portions 22. Such a configuration distributes bending (during collapse of the stent) preferentially toward the mid region of the struts. For a given stent diameter and deflection, longer struts allow for lower stresses within the stent (and, hence, a possibility of higher compression ratios). Shorter struts allow for greater radial force (and concomitant resistance to a radially applied load) upon deployment.

In order to increase stent compliance so that it compresses as much as possible, accommodation is made for the stiffer strut ends 20 provided in the design shown in FIG. 2A. Namely, the gap 24 between the strut ends 22 is set at a smaller angle as if the stent were already partially collapsed in that area. Thus, the smaller amount of angular deflection that occurs at ends 20 can bring the sections parallel (or nearly so) when the strut medial portions 22 are so-arranged. In the variation of the invention in FIG. 2A, radiused or curved sections 26 provide a transition from a medial strut angle α (ranging from about 85 degrees to about 60 degrees) to an end strut angle β (ranging from about 30 to about 0 degrees) at the strut junctions 28 and/or extensions therefrom.

In addition, it is noted that gap 24 an angle β may actually be configured to completely close prior to fully collapsing angle α. The stent shown is not so-configured. Still, the value of doing so would be to limit the strains (and hence, stresses) at the strut ends 22 and cell end regions 18 by providing a physical stop to prevent further strain.

In the detail view of FIG. 2B, angle β is set at 0 degrees. The gap 24 defined thereby by virtue of the noticeably thicker end sections 20 at the junction result in very little flexure along those lever arms. The strut medial portions are especially intended to accommodate bending. In addition, a hinging effect at the corner or turn 32 of junction section 28 may allow the strut to swing around angle α to provide the primary mode for compression of the stent.

Additional features of interest in the stent design include near and far delivery system interface mating portions 92 and 94, respectively. These elements are formed within projections 90 that may be integral to the prosthesis (e.g., when the prosthesis is constructed from a single tube of material, or when a number of wire-type elements are woven to form the body where the ends of the elements form the prosthesis). Alternatively, the projections may be affixed or connected to the stent (e.g., via welding, adhesive bonding, fastening, etc.). In another variation of the invention, the projections may comprise polymeric material that is coated onto the prosthesis 82. Other modes of construction are possible as well. Further details of the projections and respective mating portions are discussed in detail below. Suffice it to say, the elements are sufficiently "floppy" and/or rounded to offer an atraumatic interface with opposing tissue.

Figure 3A:
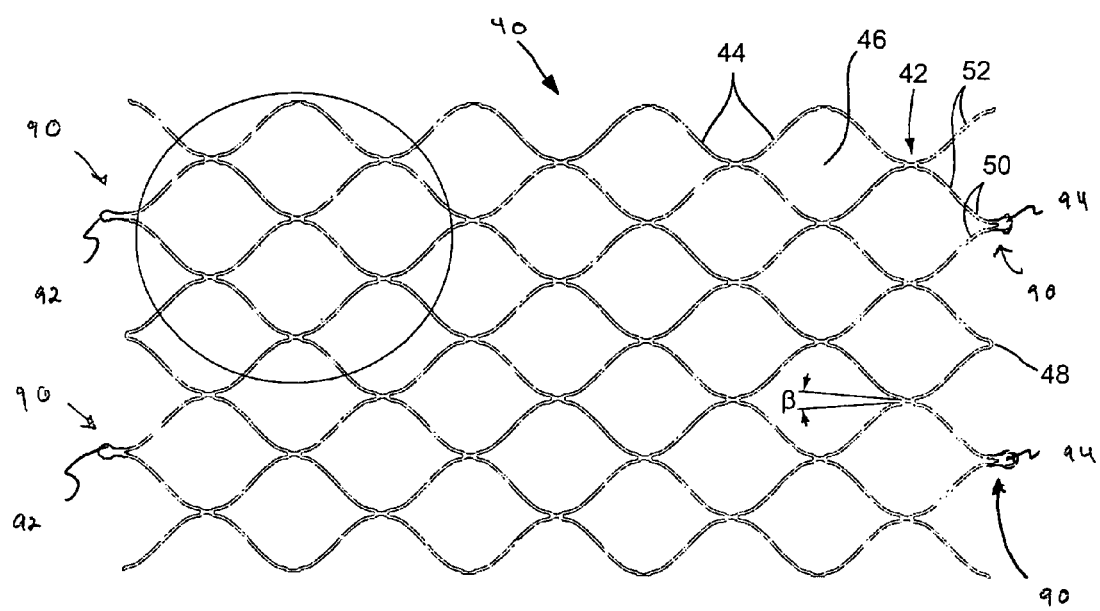
FIGS. 3A and 3B show a second expanded stent cut pattern and an expanded view of a section of the same, respectively.
Figure 3B:
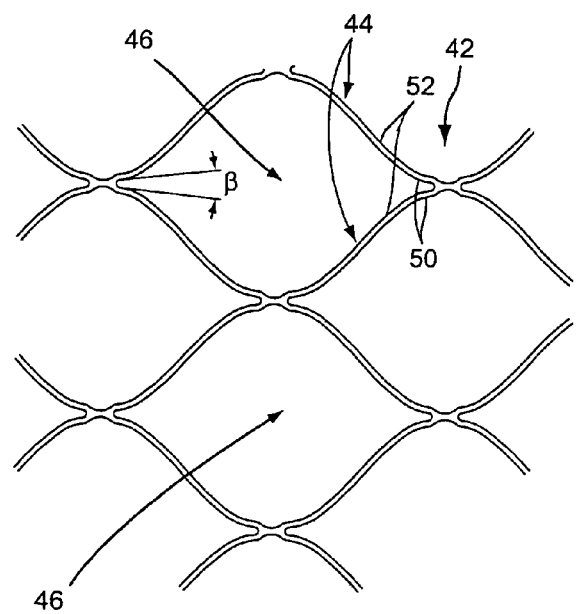

The stent pattern 40 shown in FIG. 3A and detailed in FIG. 3B offers certain similarities as well as some major differences from the stent pattern presented in FIGS. 2A and 2B. As in the variation above, the pattern includes necked down bridge sections 42 provided between adjacent struts or arms/legs 44, wherein the struts define a lattice of closed cells 46. In addition, terminal ends or crowns 48 of the cells are preferably rounded-off so as to be atraumatic, as may be projections 90 and associated delivery guide mating portions 92, 94.

Furthermore, the bridge sections 42 of stent 82 can be separated for compliance purposes. In addition, they may be otherwise modified (e.g., as described above) or even eliminated. Also, in each design, the overall dimensions of the cells and indeed the number of cells provided to define axial length and/or diameter may be varied (as indicated by the vertical and horizontal section lines in FIG. 3A).

Like the previous stent design, strut ends 50 may offer some increase in width relative to medial strut portions 52. However, as shown in FIG. 3B, as compared to FIG. 2B, the angle β is relatively larger. Such a configuration is not concerned with developing a hinge section and a relatively stiffer outer strut section. Instead, angle β in the FIG. 3A/3B design is meant to collapse and the strut ends are meant to bend in concert with the medial strut portions so as to essentially straighten-out upon collapsing the stent, generally forming tear-drop spaces between adjacent struts. This approach offers a stress-reducing radius of curvature where struts join, and maximum stent compression.

The "S" curves defined by the struts are produced in a stent cut to a final or near final size (as shown in FIGS. 3A and 3B). The curves are preferably determined by virtue of their origination in a physical or computer model that is expanded from a desired compressed shape to the final expanded shape. So derived, the stent can be compressed or collapsed under force to provide an outer surface profile that is as solid or smooth and/or cylindrical as possible or feasible. Such action is enabled by distribution of the stresses associated with compression to generate stains to produce the intended compressed and expanded shapes. This effect is accomplished in a design unaffected by one or more expansion and heat setting cycles that otherwise deteriorate the quality of the superelastic NiTi stent material. Further details regarding the "S" stent design and alternative stent constructions as may be used in the present invention are disclosed in U.S. patent application Ser. No. 11/238,646 entitled, "Small Vessel Stent Designs", filed Sep. 28, 2005 and incorporated herein by reference in its entirety.

For use in the present invention when employing a stent that is twisted down upon the delivery guide in order to reduce its diameter, it has been discovered that the design in FIGS. 3A and 3B not only compresses to a closely cylindrical profile, but that it maintains such a shape when twisted. Not to be bound by a particular theory, but it is believed that this device excels in the twisting mode because of the extremely even stress distribution it offers when simply compressed. As such, while each of the stent types shown in FIGS. 2A-3B may be employed in any of the systems described herein, the latter design may be preferred. Furthermore, the manner in which the "S" curves have been generated (as described in the incorporated patent filing) may be extended such that the analysis used to generate the as-cut (or near to as-cut) structures specifically accounts for the twist the design will be subject to in certain variations of the invention. Specifically, physical or computational models may be employed in expanding a stent from an idealized compressed state to generate the desired uncompressed stent geometry.

However derived, in order that the stent pack cleanly when twisted, it may be desired to pre-curve its shape. That is to say, the stent may be configured so that when it is twisted, its members go from a pre-twisted shape to a straightened configuration as shown. The amount of shaping to account for hold-down twist may be in the form of a simple bias or helix, S-curves or other shape(s).

Since each of the above stent designs account for problematic strain (and in the latter case actually uses the same to provide an improved compressed profile), very high compression ratios of the stent may be achieved from about 5× to about 10× or above. Moreover, they can be twisted a number of times to maintain a compressed delivery profile. The number of twists required for such action will vary depending on stent diameter and length. For a 28 mm stent sized to treat 3.0 mm vessels, between three and four twists may be desired. Similar diameter, shorter stents will require proportionally fewer rotations, as will generally smaller diameter stents.

Regardless of the design selected, it is noted that each of them exhibit a degree of foreshortening when expanding from a compressed profile. Essentially, the angle change of the struts relative to the central axis of the tubular body accounts for change in length. The amount of foreshortening experienced will, thus, depend on a combination of factors: strut length and angle as well as the number of repeating units within the design. The manner in which the resultant foreshortening is put to use in the present invention is elaborated upon below.

Before this discussion, however, it is noted that systems according to the present invention are advantageously sized to correspond to existing guidewire sizes. For example, the system may have about a 0.014 (0.36mm), 0.018 (0.46mm), 0.022 (0.56mm), 0.025 (0.64mm), 0.035 (0.89mm) inch crossing profile. Of course, intermediate sizes may be employed as well, especially for full-custom systems. Still further, it is contemplated that the system sizing may be set to correspond to French (FR) sizing. In that case, system sizes contemplated range at least from about 1 to about 2 FR, whereas the smallest known balloon-expandable stent delivery systems are in the size range of about 3 to about 4 FR. In instances where the overall device crossing profile matches a known guidewire size, they may be used with off-the-shelf components such as balloon and microcatheters.

At least when produced in the smallest sizes (whether in an even/standard guidewire or FR size, or otherwise), the system enables a substantially new mode of stent deployment in which delivery is achieved through an angioplasty balloon catheter or small microcatheter lumen. Further discussion and details of "through the lumen" delivery is presented in U.S. patent application Ser. No. 10/746,455 "Balloon Catheter Lumen Based Stent Delivery Systems" filed on Dec. 24, 823 and its PCT counterpart US824/008909 filed on Mar. 23, 824, each incorporated by reference in its entirety.

In larger sizes (i.e., up to about 0.035 inch crossing profile or more), the system is most applicable to peripheral vessel applications as elaborated upon below. Yet, even in "small vessel" cases or applications (where the vessel to be treated has a diameter up to about 3.0 mm), it may also be advantageous to employ a stent delivery system sized at between about 0.022 to about 0.025 inch in diameter. Such a system can be used with catheters compatible with 0.022 and/or 0.025 inch diameter guidewires.

While such a system may not be suitable for reaching the very smallest vessels, this variation of the invention is quite advantageous in comparison to known systems in reaching the larger of the small vessels (i.e., those having a diameter of about 2.5 mm or larger). By way of comparison, among the smallest known over-the-guidewire delivery systems are the Micro-Driver™ by Medtronic and Pixel™ systems by Guidant. These are adapted to treat vessels between 2 and 2.75 mm, the latter system having a crossing profile of 0.036 inches (0.91 mm). A system described in U.S. Patent Publication No. 2002/0147491 for treating small vessels is supposedly capable of downsizing to 0.026 inch (0.66 mm) in diameter. Furthermore, because certain of the subject devices can be used as a guidewire (in one fashion or another) after stent delivery, the present invention offers further advantages in use as elaborated upon below.

Still, as referenced above, it may be desired to design a variation of the subject system for use in deploying stents in larger, peripheral vessels, biliary ducts or other hollow body organs. Such applications involve a stent being emplaced in a region having a diameter from about 3.5 to 13 mm (0.5 inch). In which case, a 0.035 to 0.039 inch (3 FR) diameter crossing profile system is advantageously provided in which the stent expands (unconstrained) to a size between about roughly 0.5 mm and about 1.0 mm greater than the vessel or hollow body organ to be treated. Sufficient stent expansion is easily achieved with the exemplary stent patterns shown in FIGS. 2A/2B or 3A/3B.

Again, as a matter of comparison, the smallest delivery systems known to applicants for stent delivery in treating such larger-diameter vessels or biliary ducts is a 6 FR system (nominal 0.084 inch outer diameter), which is suited for use in an 8 FR guiding catheter. Thus, even in the larger sizes, the present invention affords opportunities not heretofore possible in achieving delivery systems in the size range of a commonly used guidewire, with the concomitant advantages discussed herein.

Angioplasty Balloon Lumen Based Stent Delivery

As for the manner of using the inventive system as optionally configured for "through the lumen use", FIGS. 4A-4L illustrate an exemplary angioplasty procedure. Still, the delivery systems and stents or implants described herein may be used otherwise—especially as specifically referenced herein.

Figure 4A:
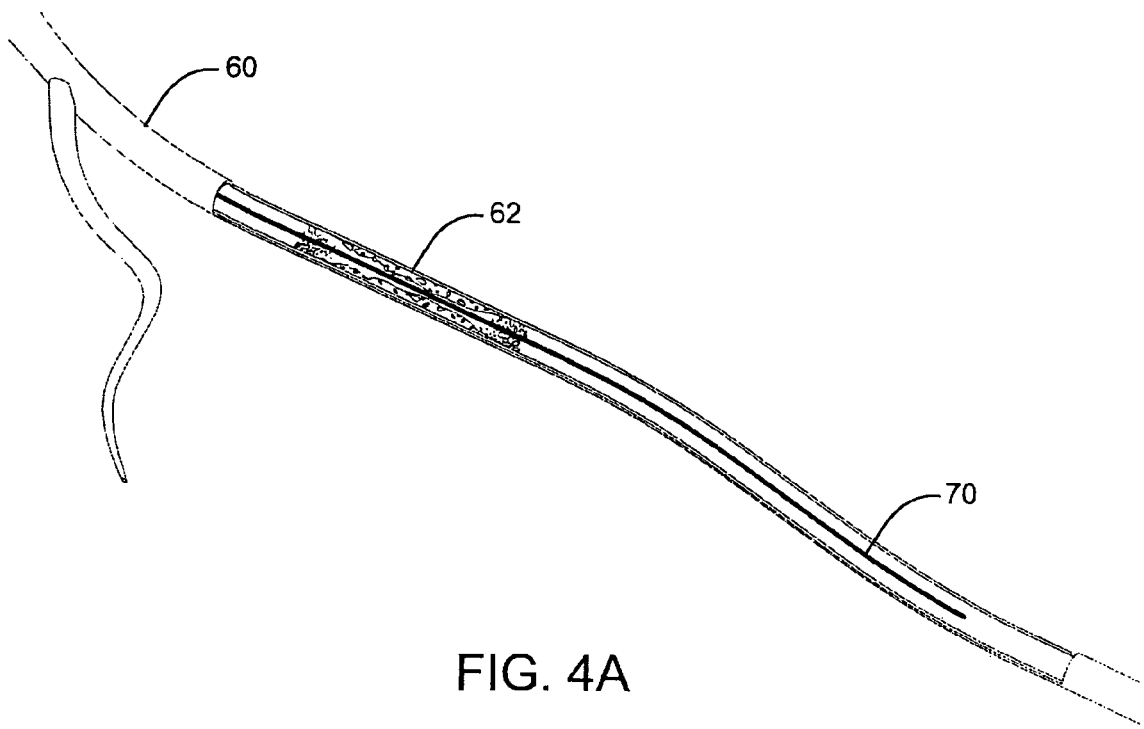
FIGS. 4A-4L show stent deployment hardware and methodology for carrying out an angioplasty and stenting procedure.
Figure 4B:
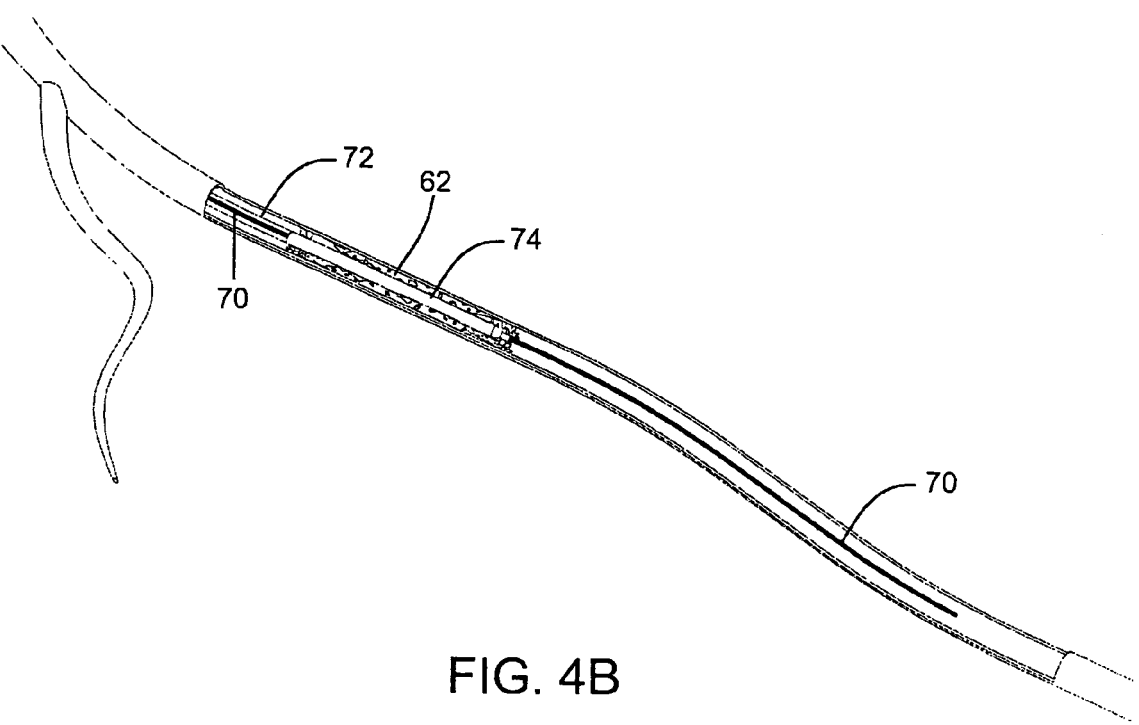

Turning to FIG. 4A, it shows a coronary artery 60 that is partially or totally occluded by plaque at a treatment site/lesion 62. Into this vessel, a guidewire 70 is passed distal to the treatment site. In Fig, 4B, a balloon catheter 72 with a balloon tip 74 is passed over the guidewire, aligning the balloon portion with the lesion (the balloon catheter shaft proximal to the balloon is shown in cross section with guidewire 70 therein).

Figure 4C:
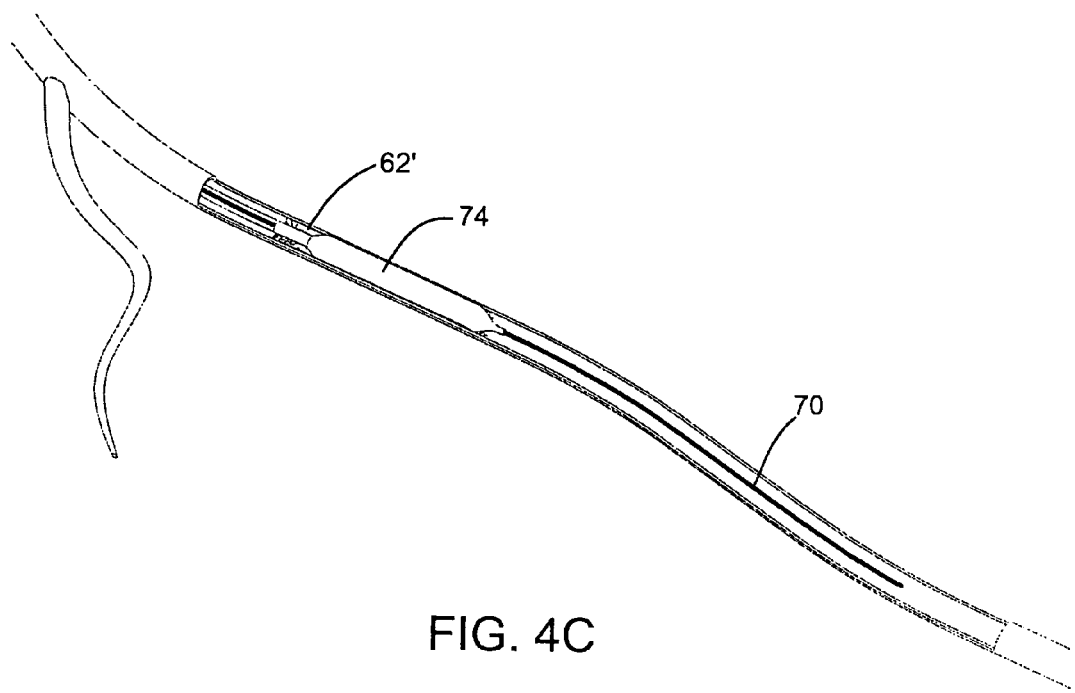

As illustrated in FIG. 4C, balloon 74 is expanded (dilatated or dialated) in performing an angioplasty procedure, opening the vessel in the region of lesion 62. The balloon expansion may be regarded as "predilatation" in the sense that it will be followed by stent placement (and optionally) a "postdilatation" balloon expansion procedure.

Figure 4D:
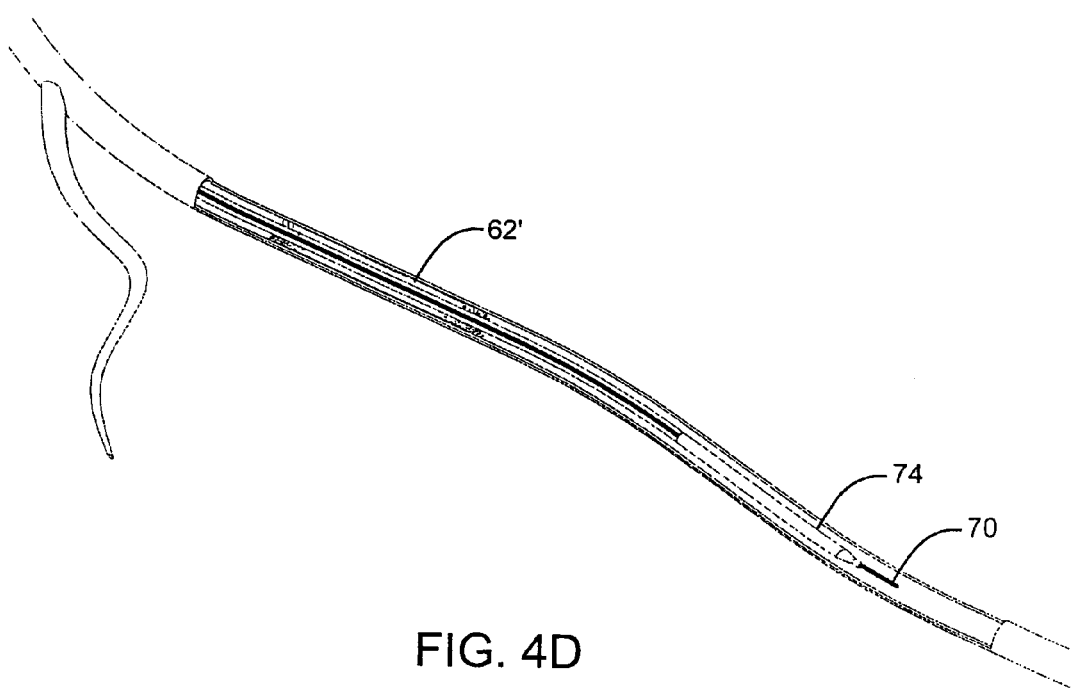
Figure 4E:
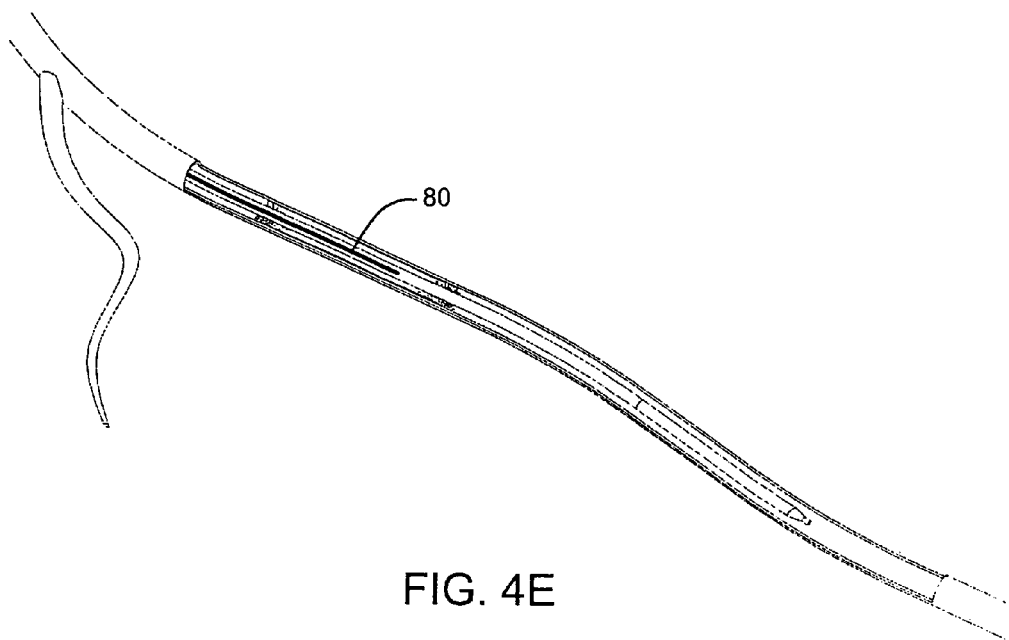
Figure 4F:
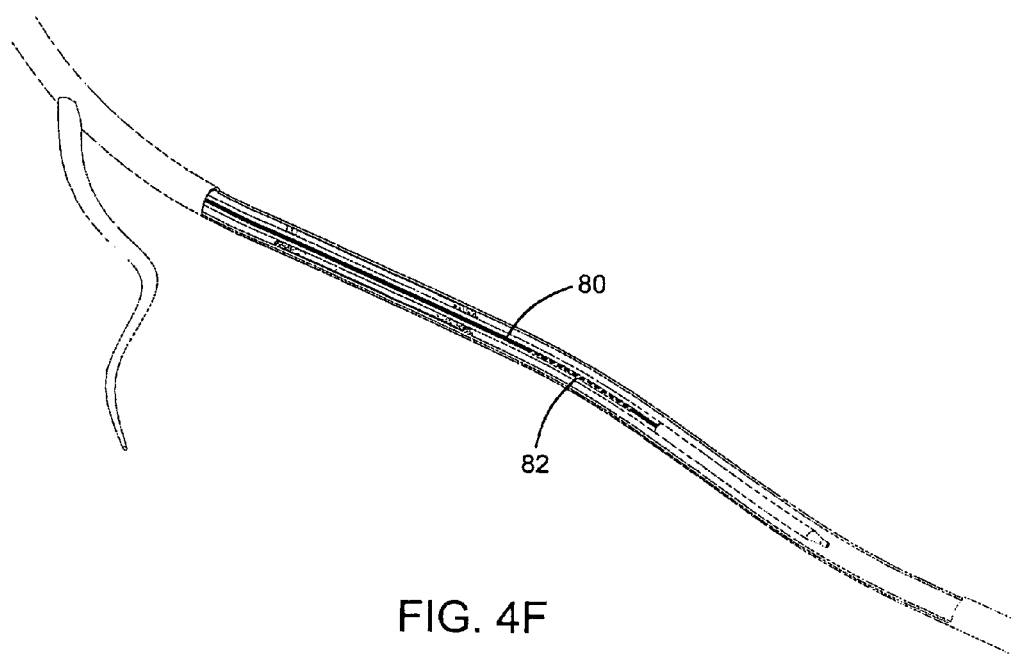

Next, for compatible systems (i.e., systems able to pass through a balloon catheter lumen) the balloon is at least partially deflated and passed forward, beyond the dilate segment 62' as shown in FIG. 4D. At this point, guidewire 70 is removed as illustrated in FIG. 4E. It is exchanged for a delivery guide member 80 carrying stent 82 as further described below. This exchange is illustrated in FIGS. 4E and 4F.

However, it should be appreciated that such an exchange need not occur.

Rather, the original guidewire device inside the balloon catheter (or any other catheter used) may be that of item 80, instead of the standard guidewire 70 shown in FIG. 4A. Thus, the steps depicted in FIGS. 4E and 4F (hence, the figures also) may be omitted.

Alternatively, the exchange of the guidewire for the delivery system may be made before the dilatation step. Yet another option is to exchange the balloon catheter used for predilatation for a fresh one to effect postdilatation.

Figure 4G:
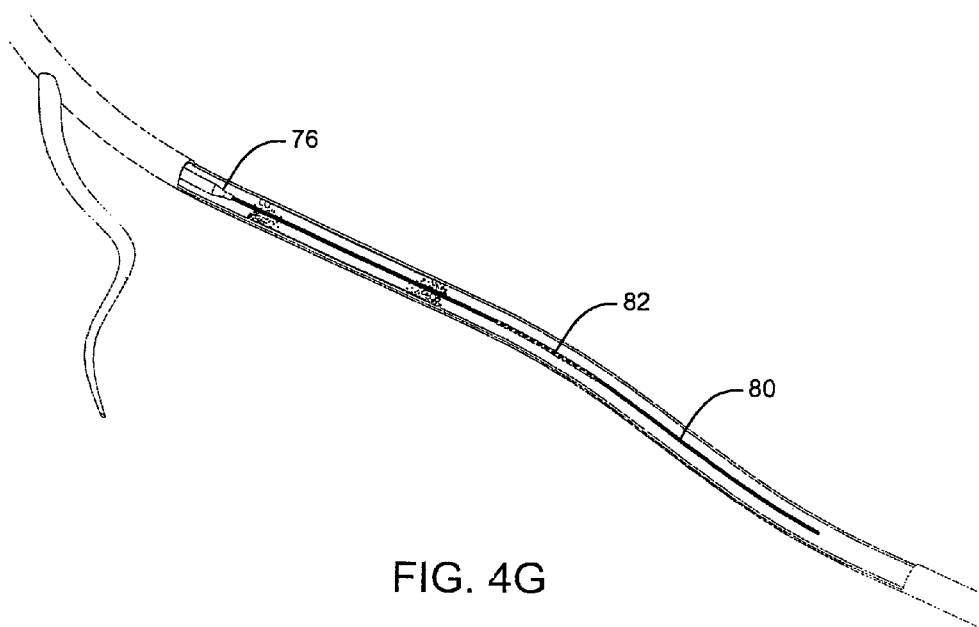
Figure 4H:
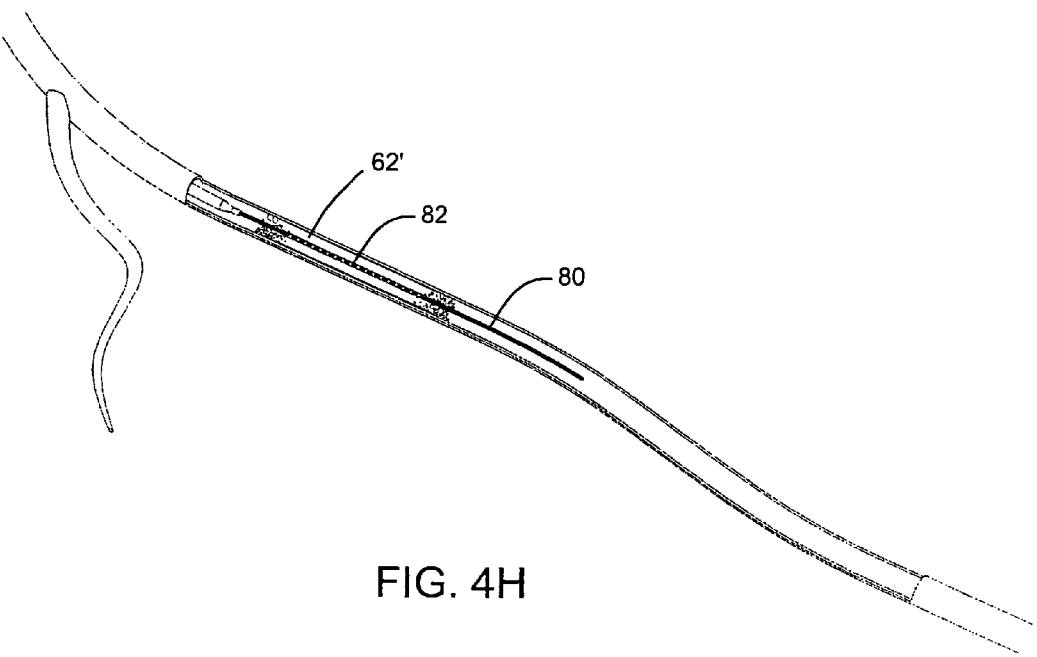

In addition, there may be no use in performing the step in FIG. 4D of advancing the balloon catheter past the lesion, since such placement is merely for the purpose of avoiding disturbing the site of the lesion by moving a guidewire past the same. FIG. 4G illustrates the next act in either case. Particularly, the balloon catheter is withdrawn so that its distal end 76 clears the lesion. Preferably, delivery guide 80 is held stationary, in a stable position. After the balloon is pulled back, so is delivery device 80, positioning stent 82 where desired. Note, however, that simultaneous retraction may be undertaken, combining the acts depicted in FIGS. 4G and 4H. Whatever the case, it should also be appreciated that the coordinated movement will typically be achieved by virtue of skilled manipulation by a doctor viewing one or more radiopaque features associated with the stent or delivery system under medical imaging.

Figure 4I:
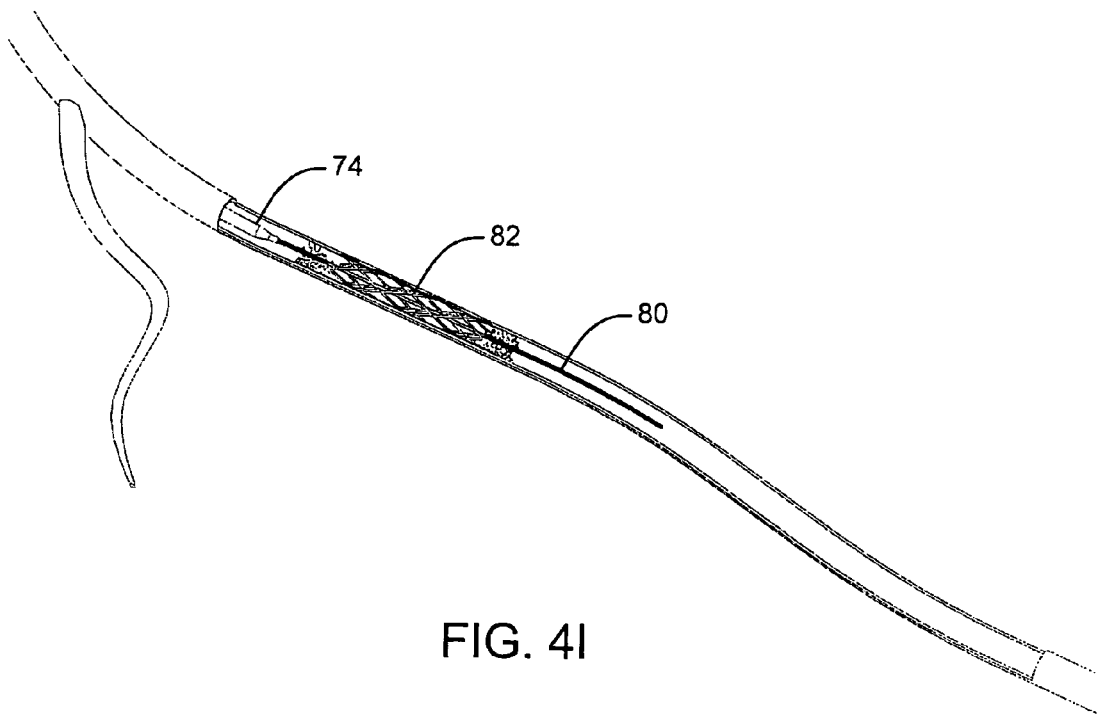
Figure 4J:
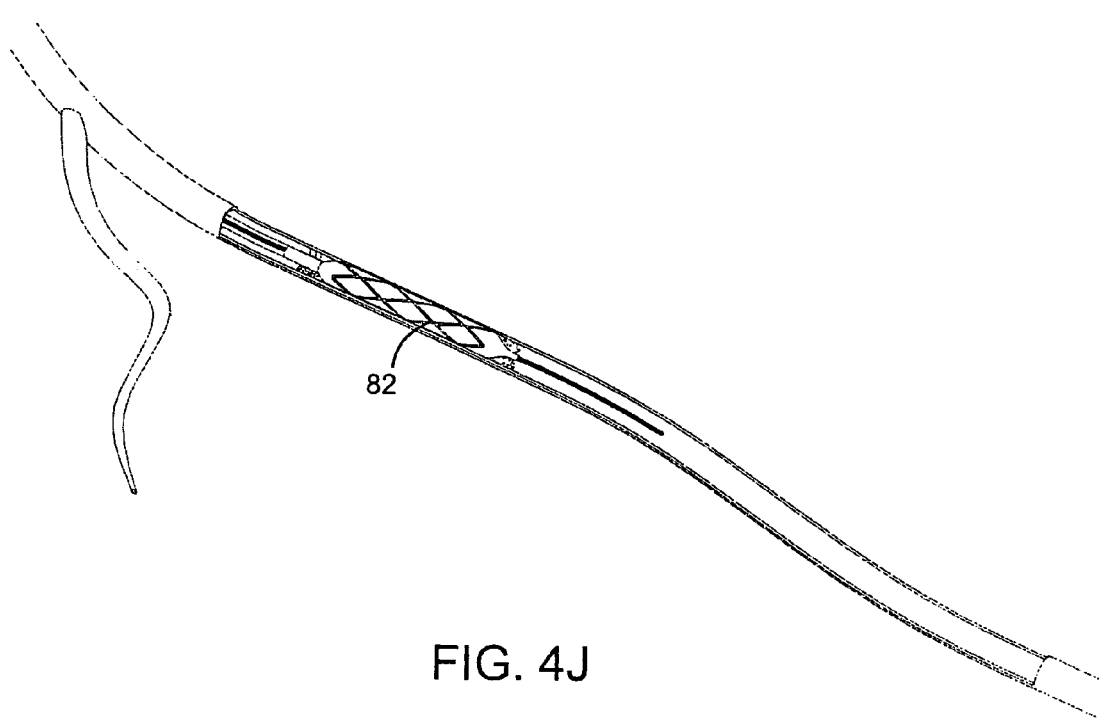
Figure 4K:
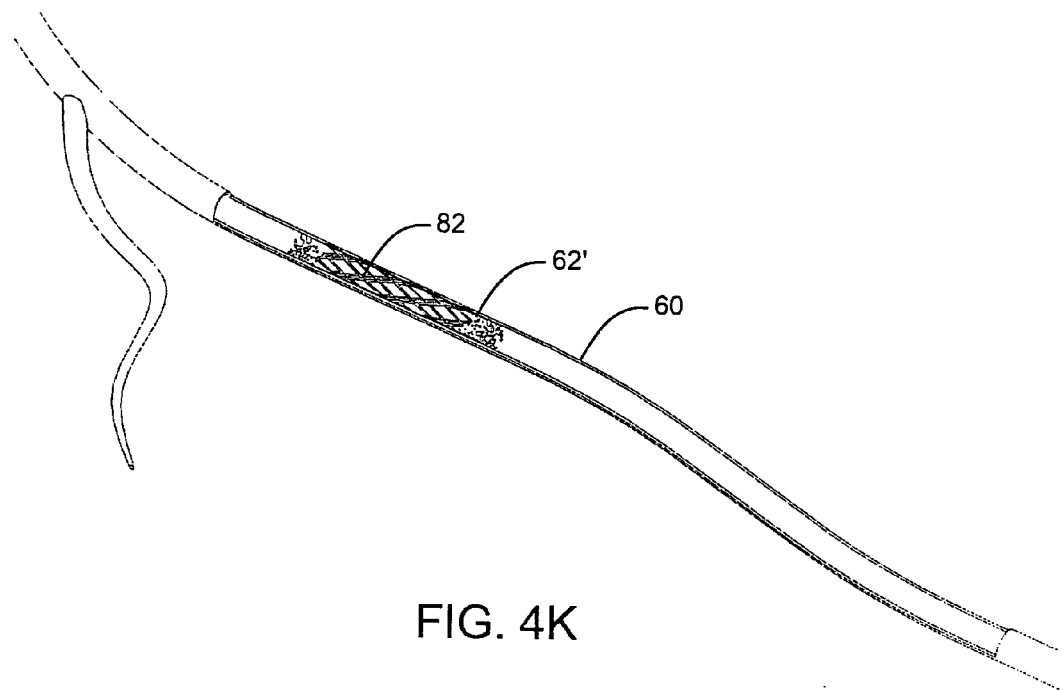

Once placement of the stent across from dilated segment 62' is accomplished, stent deployment commences. The manner of deployment is elaborated upon below. Upon deployment, stent 82 assumes an at least partially expanded shape in apposition to the compressed plaque as shown in FIG. 4I. Next, the aforementioned postdilatation may be effected as shown in FIG. 4J by positioning balloon 74 within stent 82 and expanding both. This procedure may further expand the stent, pushing it into adjacent plaque—helping to secure each.

Figure 4L:
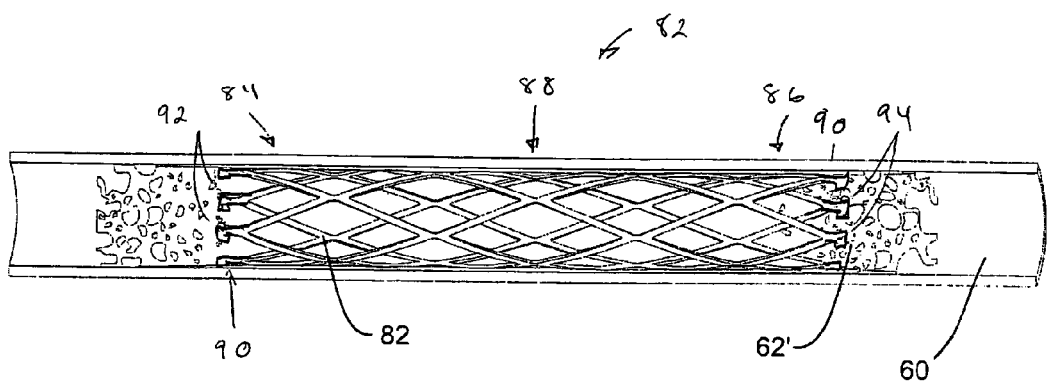

Naturally, the balloon need not be reintroduced for postdilatation, but it may be preferred. Regardless, once the delivery device 80 and balloon catheter 72 are withdrawn as in FIG. 4K, the angioplasty and stenting procedure at the lesion in vessel 60 is complete. FIG. 4L shows a detailed view of the emplaced stent and the desired resultant product in the form of a supported, open vessel.

Furthermore, it is to be recognized that the subject invention may be practiced to perform "direct stenting." That is, a stent may be delivered alone to maintain a body conduit, without preceding balloon angioplasty. Likewise, once one or more stents are delivered with the subject system (either by a single system, or by using multiple systems) the post-dilatation procedure(s) discussed above are merely optional. In addition, other endpoints may be desired such as implanting an anchoring stent in a hollow tubular body organ, closing off an aneurysm, delivering a plurality of stents, etc. In performing any of a variety of these or other procedures, suitable modification will be made in the subject methodology. The procedure shown is depicted merely because it illustrates a preferred mode of practicing the subject invention, despite its potential for broader applicability.

Stent and Delivery System Overview

Returning to FIG. 4L, the stent 82 employed in the subject delivery systems comprise a near or proximal end 84, a far or distal end 86 and a main body or support structure 88 extending therebetween. The stent 82 may further comprise projections 90. The projections 90 comprise a near mating portion 92 and a far mating portion 94 that permit retention of the prosthesis 82 on a delivery system. In one mode of operation, such retention is through twisting the stent down into a reduced profile when the ends are rotated relative to one another. In some variations of the invention, no projections need be provided; in others, they are only required on one side of the stent body 88.

A given implant may have a number of projections 90, each having various shapes rather than having a single configuration. For twist-down applications, at least two projections 90 will be provided on each side of the stent. When not every stent crown is capped by a projection, the projections are advantageously spaced substantially equally about the perimeter of the stent to evenly distribute loads upon the stent. In which case, the projections may be aligned with one another along the axis of the stent as shown in FIG. 4L or staggered about the circumference of the ends of the stent. More typically, each crown will terminate with a projection and mating features. In this manner, the stent can be fully constrained without members tending to lift-off the delivery guide in a pure twisting mode of diameter reduction for delivery. Still further, it is contemplated that the number of crowns may be reduced by taking out adjacent arm sections to turn what was a four-crown design on each end into a two-crown design. In this way, fewer projections can be used, while still providing one for every full cell at each end of the stent.

The projections may vary in length, especially depending on the form of interface or mating portion it carries or forms. The projections advantageously have a length that allow for efficiently transition or transfer twisting load to the stent while occupying minimal space. Though not necessarily excluded from the invention, projections longer than about one cell's length may have a tendency to wrap or twist about the delivery device body in attempted use.

Now that stents as optionally used in the subject delivery systems have been described, an overview of an implant delivery system according to the invention is presented in FIG. 5. Here an implant delivery system 100 is shown as including a delivery guide 102 with a handle 104, an elongate body 106 with a distal implant carrying section 108 and terminating in an atraumatic coil tip 110.

The handle may incorporate a circuit board 112 and one or more batteries (e.g., lithium ion "coin" cells) to provide power to the system's electrolytic features.

Alternatively, a power supply 116 connected by or to the delivery guide 102 by a cord 118 including one or more leads may be employed. In which case, the power supply is preferably also battery powered in that such an approach offers safety in control of current without resort to sophisticated electronics.

Irrespective of the approach employed, the electronics will be hard-wired or suitably programmed to operate to delivery a suitable power profile. Certain optional profiles as discussed below. As such, the subject power source may include such standard features as overrides and shutoffs as recognized by one with skill in the art as prudent. Further, the systems may be adapted to deliver power on one or more channels. In other words, where two electrolytic components are employed, it will be possible to power one component and corrode its member until deployment, check or monitor such deployment as evidenced by a drop-off in current, and then power another electrolytically erodable member in a staged or sequential fashion. Alternatively, every one or a selected number of electrolytic members may be powered simultaneously. However, a number of advantages as presented below are available as a result of staged deployment.

Still further, (in a configuration not shown) the handle may include one or more of a lever, slider, trigger, knob, wheel, etc. for release of any mechanical features as may be employed in a hybrid mechanical/electrical approach as referenced above. Furthermore, a removable interface member 120 may be provided to facilitate taking the handle off of the delivery system near or proximal end 122. The interface may be lockable with respect to the body and preferably includes internal features for disengaging the handle from the delivery guide. Once accomplished, it will be possible to attach or "dock" a secondary length of wire 124 on the delivery guide proximal end, allowing the combination to serve as an "exchange length" guidewire, thereby facilitating changing-out the balloon catheter or performing another procedure. Alternatively, a core member within the system may serve as an exchange-length (i.e., 300 cm) wire.

Irrespective of such options, common to the delivery guide systems is the inclusion of an electrolytically erodable release latch that releases at least one side of the implant carried by the delivery guide. A number of examples are provided below. Sections of systems are shown that can be mixed-and-matched with others (both in configurations shown and others as may be apparent to one with skill in the art).

Before describing these systems, however, it is noted that FIG. 5 also shows packaging 150 containing at least one coiled-up delivery guide 102. Packaging may include one or more of an outer box 152 and one or more inner trays 154, 156 with peel-away coverings as is customary in medical device product packaging. Naturally, instructions for use 158 may also be provided.

Such instructions may be printed product included within packaging 150 or be provided in connection with another readable (including computer-readable) medium. The instructions may include provision for basic operation of the subject devices and associated methodology. In cases where computer-readable media is provided, it may even include programming for a power supply for use in connection with a general purpose computer or more customized hardware to set and/or run the desired approach to powering activity of the delivery guide.

In support of implant delivery, it is to be understood that various radiopaque markers or features may be employed in the system to 1) locate stent position and length, 2) indicate device actuation and stent delivery and/or 3) locate the distal end of the delivery guide. As such, platinum (or other radiopaque material) bands, use of such material in constructing various elements of the subject systems, and/or markers (such as tantalum plugs) may be incorporated into the system.

Stent Loading

In certain variations of the invention, the stent is loaded upon the delivery guide in a twisted configuration. Essentially, a cage or lattice/mesh type stent assumes a decreased diameter through twisting by pulling each portion of the body of the stent across its diameter inwardly compressing the body. When the stent and delivery system offer an interlocking or keyed interface, loading of the stent is easily accomplished by engaging the interface and then pulling (thereby causing the stent to "neck" down) and/or twisting the stent into a compressed profile by rotating the seat member in receipt of the mating portions of the stent about a core member of the delivery guide.

Another approach according to the present invention is suitable for use both in instanced in which a keyed or a slide-out stent and delivery guide interface is provided. In this method, the stent is compressed by hand, with an automated "crimper" such as produced by Machine Solutions, Inc., or otherwise, without a substantial twist imparted thereto. The stent may be compressed by virtue of the act of loading it into a tube, or loaded into a tube after being compressed by a machine. In any case, the tube or sleeve that it is loaded into will generally be close in diameter to its final size when secured upon or the delivery guide. By "close" in diameter, what is meant is that it is within at least about 33%, or more preferably within about 25% to about 10%, or even within about 5% or substantially at its final diameter. Then, with the stent so-constrained, it is twisted from either one or both ends before of after partial or full attachment to the delivery guide.

The sleeve may comprise a plurality of separate pieces or segments (most conveniently two or three). As such, the individual segments can be rotated relative to one another to assist in twisting the stent. In addition, axial manipulation of the relation of thin individual segments can be employed to allow the implant to bulge outwardly over one section. The foreshortening caused by this action may then allow positioning and then axially loading end interface members by manipulating the segments to collapse the bulging.

FIGS. 6A-6F illustrate a process of loading a delivery guide using only a single restraint sleeve. To carry out the additional acts above, or to reduce the degree to which the stent must twist inside a single sleeve, sleeve 160 may be broken into a number of segments (before or after loading a compressed stent therein) as indicated by broken line.

Figure 6A:
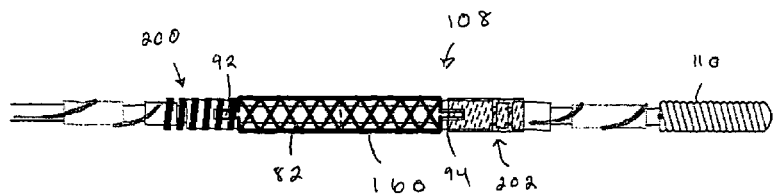
FIGS. 6A-6F illustrate hardware and methodology for loading a delivery guide with a stent in a twisted configuration.

As for the specific example of loading, FIG. 6A shows stent 82 captured within a temporary restraint 160 and set over a delivery guide distal section 108.

Its placement therein causes the stent to lengthen to about its full extent. The stent 82 includes projections serving as near and far mating portions 92, 94 interfacing with proximal seat and distal seat features 200, 202, respectively. Further details of the seat features and associated features are discussed below. Suffice it to say, here, that each of the seats may—at first—be free to rotate.

Figure 6B:
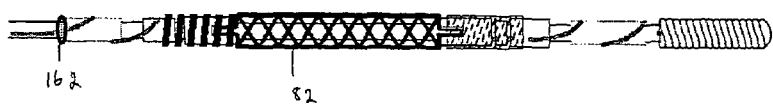

FIG. 6B shows a first glue or solder joint 162 laid-down to secure one of the seats from rotating. While the near seat 200 is the one secured, either one of them may be. The approach shown here is merely intended to be illustrative.

Figure 6C:
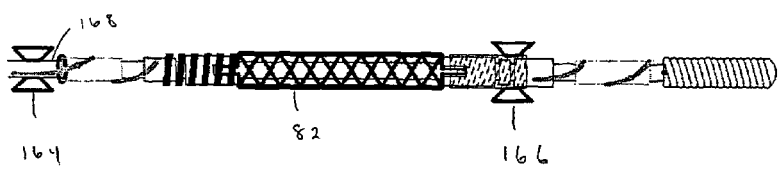

Then, as shown in FIG. 6C, clamp member 164 and 166 grasp portions of the delivery guide. The near clamp 164 grasps the body 168 of the delivery guide (though the proximal-side attachment shown in FIG. 6B could have been performed later, and the clamp attached to structure associated with the near seat 200) and the far clamp 166 holds structure associated with the far seat 202.

The clamps may comprise part of a simple twist fixture supporting chucks aligned on bearings, etc. In any case, in FIG. 6D, the clamps are rotated relative to one another (in the example illustrated, only the distal clamp is rotated because the proximal one is held stationary). As indicated by the change in the illustrated structure, the twisted stent form 82' now lays underneath restraint tube 160.

Following the twisting of the stent within the tube, the distal seat 202 is secured from counter rotation by glue or solder joint 170. Finally, clamps or chucks 164 and 166 are released and restraint 160 is cut or slid off of the delivery guide body to ready the system for stent deployment as shown in FIG. 6F.

Note, however, that the act of restraint 160 removal may take place even in the operating room as a final step prior to delivery guide use. Otherwise, it may occur as some step along the manufacturing process. When employed in the former manner, sleeve 160 will then do double duty as a loading and a storage sleeve.

Delivery Guide Implant Retention and Release Features

While FIG. 5 illustrates a full-size delivery system, a number of the following figures illustrate detail views of the far or distal end 108 of such a system. The delivery guide distal portions shown depict a number of approaches for releasably securing a stent or other implant for delivery according to the present invention. The device features are typically incorporated into complete systems and may be used in the manner described, as well as others as may be apparent to those with skill in the art.

Accordingly, FIG. 7A illustrates the stent bearing region 108 of a delivery system end including a prosthesis (e.g., a stent) 82 placed about an elongate body 180 of the delivery guide underlying in the stent. As referenced above, prosthesis 82 comprises a proximal/near end 84, a distal/far end 86 and a support structure 88 extending therebetween.

The delivery guide further comprises a number of wires or ribbons 182 passing through at least a portion of the implant 82 to secure it to the delivery guide. These members may form loops of material as shown. In any case, an erodible section 184 (indicated by the circled portion on each elongate member) serves as a releasable latch. When corroded away, the wire passing through receptacle portions at or adjacent the stent crowns is released, allowing the implant to expand.

The wire including the sacrificial material latch section may be steel or stainless steel wire. To define the sacrificial region, polyimide insulation or a protective layer of noble (or more noble) metal such as platinum or gold covered other portions of the material is stripped off (or never laid-down in the first place via a masking process) that section. The wire may be about 0.001 inch in diameter, with insulation or protective metal removed from about a 0.005 inch long section of the wire to provide the erodible section. Stainless steel wire will generally be selected for its strength and because it offers corrosion resistance "on the shelf" while being erodable in an electrolytic solution under power. Other material selection and construction options are discussed below.

As for configuration, the latch members may comprise portions of a loop of wire, as shown in FIG. 7A, which are wrapped around and secured to a delivery guide body or are passed through apertures in the delivery guide body. Solder or glue (e.g., standard medical-use epoxy or UV cure) is used to secure the ends of the material as indicated in the figure. The delivery guide body may comprise hypotube to carry one or more electrical leads 186 to the distal end of the system. In the case shown, the lead reaching to the distal connection passes through the tube then wraps back over body 180 connecting to wire 182. The lead to the proximal wires may simply ride upon the body as shown or also be received within the lumen of the hypotube.

However situated, leads 186 may be employed for connection to discrete channels or circuits of a power supply to provide individual control over corrosion of the wires. Such a setup may be desired in order to first release the distal side of the implant and then release the proximal side.

Otherwise, leads 186 may be omitted and body 180 will itself serve as the electrical conductor, in which case it will likely be covered with an insulation layer 188 or be constructed of titanium as discussed below. When the body serves as the conductor, it will be connected to the live or "hot"/positive side of a power supply. Then a hypotube outer body member or separate catheter (such as the catheter described in U.S. Pat. No. 6,059,779 to Mills) in receipt of the delivery guide can will offer the ground or negative side of the circuit. Still further, an external ground pad could be applied to the patient as known in the art. See, e.g., U.S. Pat. No. 6,620,152 to Guglielmi. When the near and far erodable sections are not electrically isolated from one another, their release may still be staged by virtue of difference in the volume or type of material to be eroded as well as by proximity of such material to "ground".

In another delivery guide configuration, the elongate body/wire may be solid and/or comprise a number of pieces 182/182' as shown in FIG. 7B. These may be soldered together and, rather than eroding an uninsulated or unprotected or less noble section of wire inserted between more noble (i.e. higher Mendelev number) sections, the solder can be electrolytically corroded to release the implant. Still, any of the options may be employed, depending on the circumstances.

For use in such a system, various stent end receptacle 190 configurations are shown in FIGS. 8A-8C. In FIGS. 8A and 8B, the receptacle is integrated with the cell structure of the stent. In FIG. 8B, the struts include an additional relieved section 192 to relieve stress from the end of the crown. In FIGS. 8C and 8D, a separate aperture 194 is provided adjacent the strut ends to receive the elongate member that passes therethrough. While the implant may not be as compact (overall) if produced in such a manner, addition benefits in term of design flexibility or performance may be realized by such an approach. An example of which may be presented in FIG. 8D which combines the features shown in FIGS. 8B and 8C.

Figure 9:
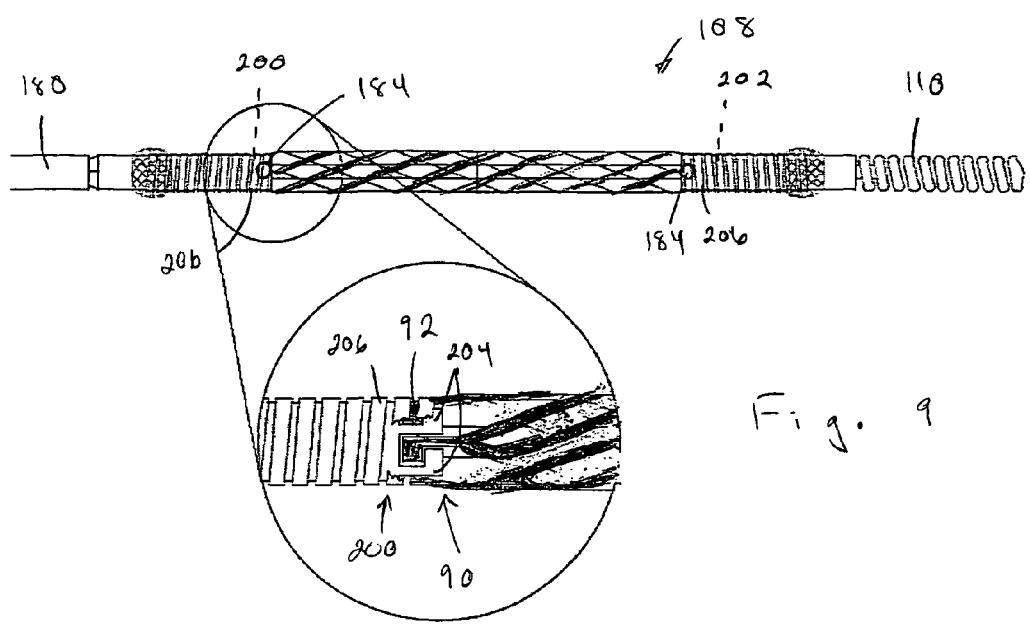
FIG. 9 shows a delivery guide variation in which the ends of a stent are capped by an erodable member.

Overall, the system shown in FIGS. 7A-8D may offer excellent advantages in terms of space-saving designs. However, there are occasions (as in when using stronger or larger stents) where it may be desirable to offer more robust hold-down features. FIG. 9 illustrates the first of a series of such structures.

The delivery guide portion 108 shown in FIG. 9 employs a stent 82 including projections 90 that are adapted for an interlocking interface with near and far seat features 204 as illustrated in the cutaway expanded view of the same figure. Here, one can observe the manner in which a wire or ribbon 206 overrides or covers the keyed interface. A proximal end of the ribbon may be secured to the delivery guide by glue, solder, etc away from the stent as illustrated. At the ribbon/ seat interface, the materials are preferably laser-welded together to best accommodate the potential delicacy of the parts.

As in the previous examples, the ribbon includes an erodible section 184. It is not connected to the stent, but it may overlay the same. Upon release of the ribbon by erosion of the erodible section (exposed to corrode by stripped insulation, etc.) the ribbon at least partially unwinds or unravels to allow projections 90 to release and the stent body to untwist and expand.

The coil, ribbon or segment that cover or overlays the interlocking feature(s) of the stent and delivery guide seat(s) serve to secure the interlocking features in engagement such that those associated with the stent cannot lift out (or be driven out) of their mates. The wrap may subtend only a small arc across the body of the delivery system or it may wrap around several times. In those several wraps, the same member may cross over the engagement features multiple times. Still, only a portion of the wrap need overlay the engaged features. Conversely, sections of more than one capture member may wrap over one or more sets of engagement features.

By including a wrap over the interlocking or interfitting features, their orientation is stabilized relative to opposing surfaces. This characteristic is of particular value when the implant secured has a torsional load or preload upon it. Even where torsional load bearing characteristics are not required, the configuration offers potential for very low-profile assembly. Strong flat ribbon can be utilized as the capture member(s). Alternatively, multiple strands of wire wound in parallel can offer the requisite strength while maintaining a low profile.

Figure 6D:
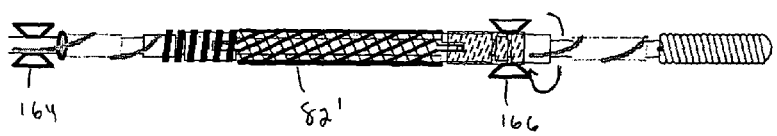
Figure 6E:
Figure 6F:
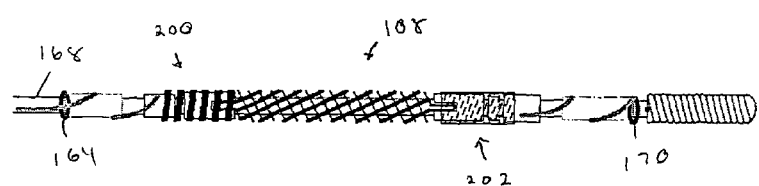
Figures 10A, 10B, 10C:
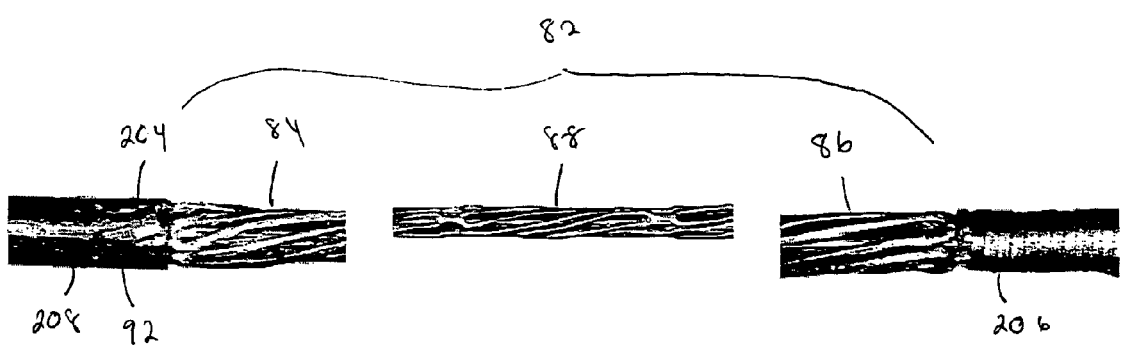
FIGS. 10A-10C, show a stent twisted-down and held in a compressed configuration.

Further, note that the system overview in FIG. 9 shows a stent twisted in the manner depicted in FIGS. 6D-6F. Photographs of a stent so-loaded on a delivery system are shown in FIGS. 10A-10C. FIG. 10A shows a proximal end 84 of a stent 82. It is held in a keyed interface by a tubular restraint 208. The stress upon the members is apparent in view of their flex. An advantage offered by the present variation of the invention is the strength offered by the cover in so-restraining the members.

While in this variation of the invention at least one of the ends of the stent will be held by an electrolytically releasable latch, one side may be mechanically released. In the case shown in FIG. 10A, such release may be effected by withdrawal of the sleeve like a sheath. Further examples are provided below, in the above-referenced "Twist-Down Implant Delivery Technologies" case incorporated herein by reference. In any case, FIG. 10B shows the manner in which the body of the stent assumes an essentially cylindrical profile with no external confinement by virtue of the twist imparted thereto. FIG. 10C shows the far end of the stent with ribbon 206 neatly securing the keyed interface.

Figure 11A:
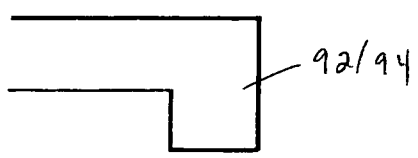
FIGS. 11A-11F show stent end variations that may be used in conjunction with delivery guide in FIG. 8 and those that follow.
Figure 11B:
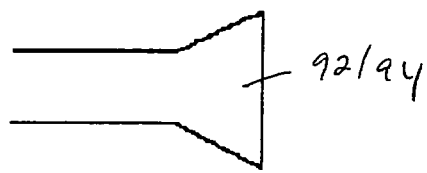
Figure 11C:
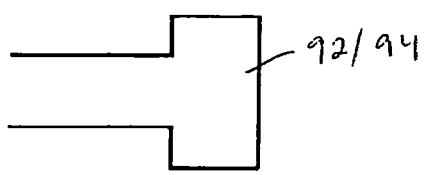

FIG. 11A provides an enlarged view of the type of mating portion employed in the delivery system just described. As partially illustrated in FIGS. 11B-11D, the mating portions may alternatively comprise shapes including, but not limited to an "L" shape, "T" shape, "V" shape, circular, oval, oblong, rectangular, square, polygonal, diamond, triangular shapes. Generally, the delivery guide seat features will offer complimentary geometry as illustrated variously throughout this disclosure. Also shown are elongate projections 90 in FIGS. 11E and 11F. These too may be employed in a delivery system such as illustrated in FIG. 9. They will not offer a locking interface of the type previously described. Yet, because they will not be axially constrained in the manner of the other mating projections, they may be used in other ways as detailed further below.

In any case, one side of the implant may include features of one type and the other side another. There may even be instances in which a mix of different projection types may be desired on a single side of the implant.

Figure 11D:
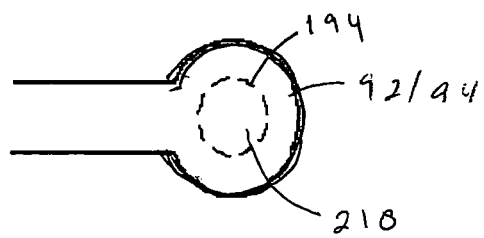
Figure 11E:
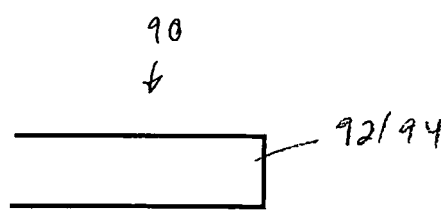
Figure 11F:
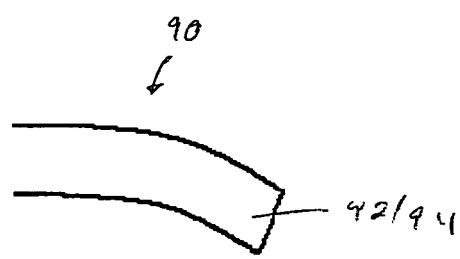

As for special features that the projections may possess, certain ones may incorporate a tantalum or platinum plug 210 for radiopacity (such as the variation in FIG. 11D), or be shaped (such as the curved variation in FIG. 11F) to account for the stresses the members will be subject to. Alternatively, a member as shown in FIG. 11D could leave aperture 194 open for use of such a projection in a wrap-through variation of the invention—such as illustrated in FIGS. 7A and 7B.

It is understood that the shape and configuration of the projection may vary for any number of factors (e.g., the particular application, the size of the stent, the tortuousity of the vasculature, etc.). As a result, the projections may comprise any hook, prong, opening, socket, key, grasper, tooth, bar or slot shaped configuration (whether the shape is nearly planar or the shape significantly extends in three dimensions) in addition to those shapes discussed herein. In accordance with the above, it follows that the corresponding seating features will be selected to receive or accommodate the shape of the respective projection. In any case, the shapes of the projections will be selected so as not to create undue risk of injury to the patient. For example, for vascular applications, the shape of the projections must be chosen so as not to create undue trauma to the vessel wall. On the other hand, non-vascular applications may not present the same risks. Accordingly, the design of the projections may be more aggressive for stents or other implants intended for such applications.

In all, the various implant/delivery guide interface features shown include captured types (via hook-in type or keyed interfaces or those that accommodate a member passing into or through an interior space) and slide-out types. The captured types offer an axial retention component at minimum. To a varying degree, they also offer lateral or radial support, where the interlocking interfaces excel in such regard. Elongate members adapted to slide out of an interface when desired are designed (together with their respective seat features) primarily to offer lateral or radial support—especially for twist-down type applications as follow.

As for more specific features pertaining to the construction of the wrapping covers to secure such relevant features, FIG. 12A shows an end sectional view of one manner of construction. Pertinent here is the manner in which ribbon 206 is fed through open regions of the seat member 200/202. This construction provides a stable interface for a weld point or well "W" to receive glue or solder (without increasing the system outer diameter) and/or a pass-through "P" allowing a full or partial wrap of ribbon 206 directly upon body core or mandrel 180 so as to take advantage of frictional forces at their interface to reduce the force that the connection point would otherwise bear.

FIG. 12B shows a distal end of a delivery system employing seats with the features shown in FIG. 12A. Here, the system is configured such that core member 180 serves as the positive electrode in the system. The seats and ribbon are all in electrical contact with this member. A hypotube body, 210 then serves as the negative or ground pole. An insulation layer 212 (e.g., in the form of a coating or tube of material) is interposed between the core member and the hypotube to prevent the system from shorting-out.

As with the variations above, where the latch members are not isolated in discrete circuits, other parameters (e.g., ribbon thickness or width at the erodable section, etc.) may be varied to manipulate release timing. And, again, because more of the system is positively charged (as opposed to the releasable members, alone) the system may require insulation to focus erosion and/or avoid current leak resulting in higher power requirements, etc.

FIG. 12C shows a variation of a near side of such a delivery guide as shown in FIG. 12B, but illustrates a different electrical connection approach (also applicable to the far side retention/release means). In FIG. 12C, the ribbon 206 is powered by a separate electrical lead 212. When the lead is insulated itself or separated from other members by insulation, and the ribbon can be completely insulated expect for its erodable section 184, then only the sacrificial material will be "hot". However, because small-size ribbon is difficult to insulate on its sides, in some cases a gold or platinum coating over the material will be employed to ensure erosion at the desired location. Then, seat 200 would also be in electrical contact with the positive side of the system. Under such conditions, seat 200 should likewise receive a protective coating (i.e., polymeric insulation or noble metal) or be made of a self-passivating material such as titanium to avoid corrosion.

To electrically isolate seat 200, ribbon 206 and any uninsulated stent loaded onto the delivery guide from core member 180 and/or hypotube 210, insulation material 210 is employed. As shown, the insulation material may comprise a plurality of tube or sleeve segments "A, B, C" in order to facilitate twisting the stent in-situ into a minimal diameter. Regardless of the manner in which it is electrically isolated, the core member and/or hypotube can then be employed as "ground" or negative component in the delivery system.

Just as any of a variety of electrical architectures can be adopted, so too are there different approaches to constructing the cover over the interface of the mating portions of the stent. FIG. 13A shows an alternate stent end cover variation 220 including electrolytically separable regions 222 joining adjacent "flower petal" sections until release. FIG. 13B shows a related construction in which wire segments 226, each with an erodible segment 184 restrain sections 224 until release.

As referenced above, the invention also contemplates systems with electrolytic release on one side of a stent and some other form of release on the other. One example is shown in FIG. 14 where a "floating" or unsecured band 230 can be driven off the seat section 200 by expansion of the stent 82 propagating from the opposite side of the stent bearing region 108 of the device. To assist this action which is driven by an increasing angle θ of the stent end the delivery guide core member 180 upon which the stent rides may be undercut or a construction provided such as shown where a band 232 provides a raised fulcrum with open space "O" behind it. Since distal-to-proximal stent deployment is often favored, it will generally be preferred that it is near seat 200 overlaid by such an automatically releasable or self-releasing cover.

FIG. 15 shows the proximal side of a distal portion 108 of a delivery guide with a tear-down cover 234 for holding and releasing the proximal end of an implant. A wire, suture or another type of rip line 236 may be situated to tear-down cover 234. The cover may include a notch 238 to assist in such action. The line may connect to a core wire 242 housed within a hypotube body 244 of the delivery guide in order to confine the mechanical action within the body of the delivery guide. Similarly, while the restraint-based capture discussed above in connection with FIG. 10A may occur by actuation of a simple sheath, it may instead be effected by an internal core wire crossing into a body tube in a manner similar to that shown in FIG. 15 or as described in U.S. patent application Ser. No. 10/991,721 entitled, "Corewire Actuated Delivery System with Fixed Distal Stent-Carrying Extension," filed Nov. 18, 2004 and incorporated herein by reference in its entirety.

While hybrid mechanical systems may certainly be employed in certain variations of the invention, another class advantageously employs two electrolytically released assemblies at the near and far end of the implant to be delivered. FIG. 16 illustrates architecture for retention and release of a first side of the implant. Other complementary structures release the second side of the implant. Since the first side of stent release is advantageously at the distal side, FIG. 16 shows the release members so-situated.

Here, a distal seat 202 is situated over a hypotube core member 250. An electrical lead wire 252 passes through the core member from a proximal end of the delivery guide to emerge to meet or define wrap section 254. Wire 252 may be a small gauge copper conductor and wrap section will comprise stainless steel with an insulative coating except at the erodible sacrificial section 184. Alternatively the same piece of stainless steel wire may serve as the electrical lead and length including the sacrificial section. The number of turns of wire 254 around the delivery guide body may vary from as few as a fraction of a turn to many (as shown). Still, at least one turn around the body may be desirable to direct force along the axis of the wire and/or take advantage of friction between the wire and delivery guide to hold position of the wire Regardless, one end of the wire may be connected to an insulative layer 256 between core member 250 and band 260. In this manner, erodible section 184 is isolated from the delivery guide body, which in operation of this variation of the invention serves as "ground" or "negative" to the extent applicable in view of the power profile selected. Band 260 is secured to seat 202 by sleeve 262. The members may be metallic and laser-welded together as indicated or otherwise connected. A blocker 264 under sleeve prevents axial movement of untwisting assembly 266.

To release the stent-received within seat 202, sacrificial latch section 184 is eroded thereby untwisting assembly 266 rotates. The rotation causes the associated stent to untwist and expand. The expansion results in foreshortening that pulls the stent's distal projections out of capped slot 268.

Untwisting assembly 266 is advantageous, among other reasons, because it requires no translation to operate; the assembly simply rotates to effect release. As such, it offers an extremely robust operation in even the most tortuous anatomy.

Still, a pair of sleeve sections 262 and 262' may be provided as indicated by broken line. The near section 262' would then be set to slide back for stent release in a manner similar to the approach taught in connection with FIG. 14 with sleeve 230. The other would still be used to connect band 260 and seat 202.

FIGS. 17A and 17B illustrate another retention and release approach employing an unwinding assembly 270—typically for use at a proximal end of a delivery guide. Here, a ribbon 206 is connected to a band 256 and a seat 200 secured against rotation by a wire 252/254. Upon release of a sacrificial section 184 of the wire, the band and seat can rotate relative to one another, to the extent that the ribbon expands. So configured, the ribbon is able to open some amount to aid in releasing the near projections from the stent. Different states of the ribbon 206, the erodible wire 252/254 and proximal seat 200 are illustrated in each of FIGS. 17A and 17B showing restraining and release states, respectively.

A blocker (like blocker 264) can be set within gap "G" to stabilize band 256 and allow seat 200 to travel in a distal direction to reduce the ribbon diameter upon withdrawal. Another blocker can be set distal to seat 200 to limit such travel as indicated in phantom line. However, it may be desirable to allow the member to "float" so that, upon withdrawal of the system, the distal movement of seat 200 pulls ribbon 206 into a reduced diameter.

FIG. 18 shows a distal portion of a stent delivery guide, together with a stent 82 employing a proximal unwinding assembly 270 and distal untwisting assembly 266 for stent retention and release. Of course, other delivery guide combinations of retention/release assemblies may alternatively be provided.

FIG. 19 shows a system employing an untwisting assembly 266 and a covered key interface like that illustrated in FIGS. 13A and 13B. This system may be desirable from the perspective of maintaining a positive lock on the implant until proximal release is desired. Therefore, the system can be withdrawn (with the stent attached thereto) most easily in case emergency withdrawal is required.

FIG. 20 shows another advantageous system. It employs an untwisting assembly 266 at a far end of the stent-bearing region 108, and a simplified proximal seat interface 272 on the near side. Seat 200 is merely covered by a sleeve 274. To effect final stent delivery, with the stent distal side 86 seated against the vessel wall, the delivery guide is simply withdrawn so that the near stent projections slide out. Of course, if the retention/release components were reversed, then advancing the delivery guide would finalize delivery. Yet, (as shown) the system may advantageously employ the leading edge 276 of a catheter body 278 to help urge the stent from the slotted interface 268.

Yet another class of delivery systems according to the present invention employing an untwisting assembly 266 is shown in FIGS. 21A and 21B. These figures illustrate two states of a distal portion of a delivery guide that employ a self-locking/auto-releasing proximal spring-spring back assembly 280.

Spring-back assembly 280 includes a coil spring 282 or a similar member that is wound-down upon the delivery guide body portion 284 when the stent is fully twisted. As wound, the position of the spring is locked. However, when untwisting assembly 266 allows the stent to unwind, spring 282 follows, and its coils expand. As the coils expand, the spring withdraws seat 200. As such, it pulls seat 200 off of the stent some distance "D". One or more blocker members can be provided to maintain the proximal position of the stent for this withdrawal. Alternatively, the spring may withdraw sleeve 262 alone such that the seat is left uncovered by action of the spring.

FIGS. 22A and 22B show a somewhat related system to that in FIGS. 21A and 21B. It also employs an untwisting assembly 266 unlocking a coil spring 282 for retracting a member. FIGS. 22A and 22B show two states of the delivery guide. In the first, a restraint covers the stent-bearing region 108. Upon unlocking the spring as a result of releasing assembly 266, the restraint is withdrawn, releasing the stent that is at least partially abutted by stop or blocker member 286.

As indicated by the broken line, the restraint 284 may cover the whole stent or only some portion thereof. Where only a partial restraint sleeve is used, the stent will be twisted down in diameter distal to the edge of the restraint. It may also lie twisted under the restraint. When a restraint covering the entirety of the stent is employed, the stent may or may not be twisted—though at least the restraint and coil assembly will be twisted relative to the delivery guide body and assembly 266 to effect the lock/unlock approach described.

FIG. 23 shows another delivery guide variation employing a tubular sleeve. As above, sleeve 290 may be in the form of a pull wire actuated restraint or a full sheath. In this variation of the invention, the stent 82 is generally not twisted, but rather only compressed within the sleeve. A blocker may optionally be provided, but is not necessary in that a far end 86 of the stent is held by an electrolytically releasable band covering a keyed interface. This approach stabilizes the end of the stent for delivery.

An advantage of such a system is to reduce the force by which the stent pushes against the sleeve, thereby lowering (at least initial) sleeve withdrawal forces. After initial movement of the sleeve, the far end of the stent may be released so that the expansion of the stent helps drive the sleeve off the body 88 of the stent. In which case, blocker 286 will be necessary to stabilize the near end 84 of the stent in completing sleeve 290 withdrawal. In another approach, the ribbon is not electrolytically released until after complete sleeve withdrawal.

FIGS. 24A and 24B show preloaded spring-back restraint systems. In each, a coil spring, elastomeric tube, or relived metal (e.g., NITINOL) tube (as shown) serves as a spring 292 to withdraw a sleeve 294 restraining a stent in a compressed profile. The spring is preloaded under tension to offer a return stroke upon release. In the variation shown in FIG. 24A, a wire latch 296 with a sacrificial erodible section 184 is provided to hold the structure in its preloaded condition until release. The sleeve 294 will generally comprise a polymeric tube. Therefore, a reinforcing band 298 to receive the latch wire may be desired so as to insure the system does not inadvertently release. The system in FIG. 24B resembles that in FIG. 24A, except in that an erodible solder connection 300 between the delivery guide core 250 and at least a portion of the spring acts to pin the system in a preloaded configuration until erosion of the material and release upon applying power. Further, it is to be understood that other approaches may be utilized to restrain and then release a spring-loaded sleeve for stent delivery.

Erosion Control

In describing the various systems above, some discussion was offered as to which elements are insulated from one another or shielded from corrosion by noble metal. Certain details regarding the same are readily understood by those with skill in the art. Generally speaking, however, numerous ones of the above systems illustrate separate lead wires to actuate the electrolytically erodible release means. Likewise, many of the systems include separate lead wires to actuate the proximal electrolytically erodible release means. By providing separate circuits, especially in instances in which the body of the device serves as a return path, the latches can be actuated individually. Their action can be monitored. When current no longer flows on a given circuit, positive indication is offered that the subject latch has been released. Furthermore, the latches can be released individually without unintended early release of one relative to the other as is possible in systems which simply rely on the volume of material to be eroded. Another beneficial factor is that by eroding one latch at a time, current is limited relative to a system in which multiple sections of material would be eroded at once.

In certain variations of the invention, isolation of one member from another in order to isolate their respective polarities is accomplished through the use of interposed polymer tubing or coatings. However, one aspect of the invention contemplates systems in which little insulation is employed, and rather system components intended to be protected from corrosion are made from titanium. Those members which are to be set for erosion are to be made of stainless steel or another suitable material. The sacrificial material may be a section of material connected to or interposed between one or more titanium sections of material by laser welding, resistance welding, soldering, etc. Otherwise, some portion of the system may comprise titanium, while the ribbon, wire or other member including a sacrificial section consist substantially of one material (such as stainless steel) and the rest is covered by insulation or a noble metal protective coating.

Other components not to be eroded are made of anodized titanium. With the anodized layer, the material is far less susceptible to erosion. What is more, upon application of voltage, small nicks or scratches in the titanium will passivate (become anodized) given a voltage applied of about 3V or more. Some current drain will be experienced, but the major site for ion transfer will be at the section intentionally left bare.

Electrical Safety Architecture

In yet another aspect of the invention bi-polar systems are provided in which the referenced "hot" and ground sections are in close proximity to one another. By limiting the distance over which ion travel must occur to transfer charge/pass current, the spread of electrical lines of flux are minimized. The graphic of FIG. 25 illustrates this effect. Generally, one aspect of the invention involves minimizing the separation between an electrolytically erodible section 184 and return path 302. The separation "S" is desirably within 1 cm distance. More preferably, it is within 5 mm to 1 mm distance or less. In this manner, the amount of potential electrical penetration in a 2 to 3 mm vessel is minimized.

Electrical Performance

Electrolytic erosion of a section of metal on a delivery system element to release an implant is driven by applying voltage to develop a positive charge on the element resulting in a strong motive force to cause current to flow to a negatively charged body. The mechanism by which current flows is ion transfer from the section to be eroded. Further discussion of this process is described and/or relates to the mode of release in various patents including U.S. Pat. No. 5,122,136 to Guglielmi; U.S. Pat. No. 6,716,238 to Elliot; U.S. Pat. No. 6,168,592 to Kupiecki, et al.; U.S. Pat. No. 5,873,907 to Frantzen and the multiplicity of continuation, continuations-in-part and divisional applications related to these patents.

In the present invention, a DC voltage component is likewise applied to effect corrosion/erosion of the implant release means. And while adding an AC voltage component for sensing purposes is known (e.g., as described U.S.Pat.No. 5,569,245 to Guglielmi, et al.; U.S. Pat. No. 5,643,254 to Scheldrup, et al.) the invention hereof does so and uses the AC voltage in a very different manner.

Specifically, it has been appreciated that use of significant AC component offset by a DC signal can dramatically improve the process of implant delivery through electrolytic corrosion. Not to be bound by a particular theory, but it is thought that efficiency gains are related to controlling blood electrocoagulation and to having periods of higher peak voltage during the upsweep of the AC signal.

This AC component is especially beneficial in coronary therapy because high frequency (e.g., 10 kHz to 100 kHz or greater) AC power does not effect heart rhythm unless the waveform becomes unstable. Controlling electro-coagulation is very important for safety reasons (in avoiding emboli formation that could lead to stroke or other complications) and also to increase the speed of corrosion.

Generally speaking, while corroding a positively charged section of metal, the positive charge attracts negatively charged blood cells which coagulate on the surface of the metal. The coagulated blood cells cover the corroding metal and slow the deployment process. Higher DC levels can be employed to push past this effect, but for safety considerations (especially in the vicinity of the heart) it is desirable to use lower DC voltages.

Instead, when an AC signal is employed that drops the trough of the waveform into the negative regime, an opportunity exists to repel the negatively charged blood cells. The resulting decrease or lack of electrocoagulation offers an efficiency increase so that DC voltage can be dropped while maintaining deployment times that are subjectively acceptable to a medical practitioner (e.g., less than about 1 minute or about 30 seconds).

Power is preferably delivered to the subject systems employing a custom battery-powered power supply. Still, various function generators may be employed for experimental purposes. A Fluke model PM 5139 Function Generator proved adequate in practicing the subject invention. A square wave function is most advantageously employed to maximize the time spent at peak and minimum voltage levels, but sinusoidal, saw-tooth, and other variations of these forms may be employed. Still further, frequency modulated waveforms in which more or less time is spent in the positive or negative regimes may be employed.

Regardless of how it is generated, FIG. 26 shows an exemplary power profile as may be used with the current invention. The Figure shows a square wave at about 110 kHz with a 10V peak to peak (10Vpp) AC component that is offset by a 2.2V DC signal." This results in a square wave with a 7.2V peak and −3.8V trough. Through testing is has been appreciated that such a power profile erodes sacrificial material in an electrolytic solution much faster than would DC signal alone. Indeed, testing has shown that using DC voltage alone at steady state voltages below 2.5V results in very long erosion times (i.e., upwards of 2 minutes to erode 0.003 inch diameter wire) and providing power at 2V will often not erode stainless steel wire at all. With the addition of an AC profile of at least 4Vpp, however, the DC component could drop to as low as about 1V to about 1.5V giving a resulting waveform with a peak from 3 to 3.5V and a trough from −1 to −0.5V and still offer an acceptable rate of corrosion.

In porcine blood, it was determined that a peak waveform voltage of above 8V begins to cause electrocoagulation, even with trough voltages of −6 to −7V. The level of electrocoagulation varies with the level of the DC component and the size of the piece of metal to be eroded, but usually the peak voltage should remain below 9V and most often below 8V to avoid appreciable electrocoagulation.

In view of the above, and further for safety reasons—especially in the vicinity of the heart—it may be desirable to maintain the DC component of the power applied between about 1 and about 5V, and more preferably between about 1.75 and about 3V, and possibly most preferably between about 2 and about 3V. The AC waveform employed will generally then be selected to generate a peak below about 9V and usually below about 8V, with 7-7.5V being typical per the above. Accordingly, the resultant power profile may have a peak or maximum between about 4 and about 9V, and a minimum of about −0.5 to about −5V. Within this range (and in certain circumstances, outside the range, given situations where some amount of electrocoagulation is acceptable), more effective combinations exist as detailed herein and as may be apparent to those with skill in the art in review of the present disclosure.

EXAMPLE 1

The impact of AC voltage on actual erosion/corrosion rates during bench tests of tensioned .002" stainless steel wire was conducted. Setups were provided in which an insulated wire was equally tensioned and exposed along a 0.020 inch long section. The wires were placed in 38° porcine blood and power was applied. When applying 2V DC, it took 3-4 minutes to break the wire. When applying 2V DC and 10Vpp AC, time to separation ranged from 20-30 seconds. The setups tested under DC-only conditions were observed to generate roughly 0.040 inch balls of electrocoagulation on the ends of the wire opposite the eroded section. In marked contrast, the AC/DC power driven setups showed no visible electrocoagulation.

EXAMPLE 2

The same test piece setup described in Example 1 was used with a lower DC voltage. With only 1V DC the wire would not break even after 15 minutes of applied power. When a 10Vpp AC signal was added to the 1V DC signal, the sample test section broke in roughly 1 minute.

EXAMPLE 3

Tests were conducted to determine the improvement offered over the power supply provided by Target Therapeutics for detatching GDC® coils. First a comparative model was developed. The electrolytic "joint" in a GDC system was determined to be about a 0.005 inch long, 0.003 inch diameter stainless steel wire. In 38° porcine blood, with the Target Therapeutics power supply set at a 1mA currently delivery setting, voltage metered by the power supply initially showed at 3V, rose to 6.5V for the majority of the deployment time, and then rose to 8V. Over a deployment time measured at 40 seconds, the average voltage observed was about 6.5V. In addition, a ball of electrocoagulation having about a 1/32 inch diameter was observed.

A "test joint" model was developed to compare a number of samples in performance. It employed a roughly identically sized exposed wire extension as described above, but no occlusive coil attached thereto. In eroding the wire extension with the Target Therapeutics power supply set at a constant 1mA current, significant variability about the above referenced GDC test results was observed. Voltage varied over a greater range from 1.9V to 9V. Time to complete erosion ranged from 40-50 seconds irrespective of such variance. Average voltage was about 4V. Electrocoaguation was observed on all samples. In instances where voltage climbed to about 6V, similarly large 1/32 inch diameter balls of electrocoagulation were observed. When applying a 2.5V DC with 10Vpp AC signal to test joint systems, current floated between 0.5 and 0.75ma. Deployment times were consistently about 50 seconds. No electrocoagulation was visible upon inspection.

Variations

The invention includes methods that may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that a lubricious coating (e.g., hydrophilic polymers such as polyvinylpyrrolidone-based compositions, fluoropolymers such as tetrafluoroethylene, hydrophilic gel or silicones) may be placed on the core member of the device, if desired to facilitate low friction manipulation. The same may hold true with respect to method-based aspects of the invention in terms of additional acts as commonly or logically employed.

In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language.

That being said, we claim:

1. A method of maintaining a self-expanding stent on a delivery guide, the method comprising:
   twisting a stent, which comprises a lattice of closed cells, to a reduced profile, wherein the stent comprises a plurality of near end projections and a plurality of far end projections, wherein the stent is releaseably secured to a delivery guide through said projections, and wherein twisting the stent comprises rotating the near end projections or the far end projections relative to other; and
   holding the stent twisted by maintaining at least one rotatable seat in a fixed position, wherein the at least one rotatable seat is secured to the delivery guide and coupled to the near end projections or the far end projections the stent.

2. The method of claim 1, wherein maintaining the at least one rotatable seat in a fixed position comprises maintaining the at least one rotatable seat in a fixed rotational position relative to the delivery guide.

3. The method of claim 2, wherein maintaining the at least one rotatable seat in a fixed position comprises maintaining the at least one rotatable seat in a fixed position with a member having an electrolytically erodable sacrificial section.

4. The method of claim 3, wherein the far end projections are coupled to said at least one rotatable seat and said near end projections are releasably secured to another seat coupled to the delivery guide and a second member is wrapped around the another seat and at least a portion of the near mating portion.

5. The method of claim 1, wherein the delivery guide has a crossing profile in the range of about 1 French to about 2 French.

6. The method of claim 1, wherein allowing the stent to untwist and expand causes the length of the stent to shorten.

7. The method of claim 1, wherein the delivery guide is a guidewire.

8. The method of claim 1, wherein each closed cell comprises a plurality of struts including a first pair of axially adjacent and interconnected struts and a second pair of axially adjacent and interconnected struts, one strut of the first pair being connected to the one strut of the second pair through a strut junction.

9. The method of claim 1, wherein each closed cell consists of four interconnected struts.

* * * * *